United States Patent
Utley et al.

(10) Patent No.: US 7,468,060 B2
(45) Date of Patent: *Dec. 23, 2008

(54) SYSTEMS AND METHODS FOR TREATING OBESITY AND OTHER GASTROINTESTINAL CONDITIONS

(75) Inventors: David S. Utley, Redwood City, CA (US); Rachel E. Croft, San Francisco, CA (US); John Gaiser, Mountain View, CA (US)

(73) Assignee: Respiratory Diagnostic, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/291,862

(22) Filed: Nov. 8, 2002

(65) Prior Publication Data

US 2004/0089313 A1 May 13, 2004

Related U.S. Application Data

(63) Continuation-in-part of application No. 10/155,294, filed on May 24, 2002, now Pat. No. 6,712,074, which is a continuation of application No. 09/304,750, filed on May 4, 1999, now Pat. No. 6,402,744, which is a continuation-in-part of application No. 09/026,296, filed on Feb. 19, 1998, now Pat. No. 6,009,877, application No. 10/291,862, which is a continuation-in-part of application No. 10/156,505, filed on May 28, 2002, which is a continuation of application No. 09/410,448, filed on Oct. 1, 1999, now Pat. No. 6,405,732.

(51) Int. Cl.
*A61B 18/18* (2006.01)
*A61N 1/00* (2006.01)

(52) U.S. Cl. .......................... 606/41; 607/133; 128/898
(58) Field of Classification Search ................. 128/898; 606/41, 42, 45–50, 90; 607/101, 115, 116, 607/133
See application file for complete search history.

(56) References Cited

U.S. PATENT DOCUMENTS

| | | | |
|---|---|---|---|
| 4,403,604 A | 9/1983 | Wilkinson et al. |
| 4,592,339 A | 6/1986 | Kuzmak et al. |
| 5,074,868 A | 12/1991 | Kuzmak |
| 5,160,338 A | 11/1992 | Vincent |
| 5,226,429 A | 7/1993 | Kuzmak |
| 5,263,480 A | 11/1993 | Wernicke et al. |
| 5,403,326 A | 4/1995 | Harrison et al. |
| 5,540,734 A | 7/1996 | Zabara |
| 5,601,604 A | 2/1997 | Vincent |

(Continued)

FOREIGN PATENT DOCUMENTS

EP 0 334 086 9/1989

(Continued)

*Primary Examiner*—Michael Peffley
(74) *Attorney, Agent, or Firm*—Ryan Kromholz & Manion S.C.

(57) ABSTRACT

Systems and methods affect tightening of the pyloric sphincter and/or serve to mediate or moderate receptive relaxation of muscles in the stomach, to treat or mitigate various physiologic conditions, such as obesity, biliary reflex, GERD, and/or Barrett's esophagus. The systems and methods may be used as either a primary treatment modality, or applied as a supplementary treatment before, during or after a primary intervention.

28 Claims, 26 Drawing Sheets

U.S. PATENT DOCUMENTS

| | | | | |
|---|---|---|---|---|
| 5,690,691 | A | 11/1997 | Chen et al. | |
| 5,836,994 | A | 11/1998 | Bourgeois | |
| 5,957,920 | A * | 9/1999 | Baker | 606/33 |
| 6,006,755 | A * | 12/1999 | Edwards | 128/898 |
| 6,014,579 | A | 1/2000 | Pomeranz et al. | |
| 6,044,846 | A | 4/2000 | Edwards | |
| 6,056,744 | A | 5/2000 | Edwards | |
| 6,077,257 | A * | 6/2000 | Edwards et al. | 604/506 |
| 6,092,528 | A | 7/2000 | Edwards | |
| 6,197,022 | B1 | 3/2001 | Baker | |
| 6,254,598 | B1 | 7/2001 | Edwards et al. | |
| 6,405,732 | B1 * | 6/2002 | Edwards et al. | 128/898 |
| 6,419,673 | B1 | 7/2002 | Edwards et al. | |
| 6,427,089 | B1 | 7/2002 | Knowlton | |
| 6,464,689 | B1 | 10/2002 | Qin et al. | |
| 6,464,697 | B1 | 10/2002 | Edwards et al. | |
| 6,540,789 | B1 | 4/2003 | Silverman et al. | |
| 6,544,226 | B1 | 4/2003 | Gaiser et al. | |
| 6,547,776 | B1 | 4/2003 | Gaiser et al. | |
| 6,558,400 | B2 * | 5/2003 | Deem et al. | 606/151 |
| 6,589,238 | B2 | 7/2003 | Edwards et al. | |
| 6,645,201 | B1 | 11/2003 | Utley et al. | |
| 6,699,243 | B2 | 3/2004 | West et al. | |
| 6,733,495 | B1 | 5/2004 | Bek et al. | |
| 6,783,523 | B2 | 8/2004 | Qin et al. | |
| 6,790,207 | B2 | 9/2004 | Utley et al. | |
| 6,802,841 | B2 | 10/2004 | Utley et al. | |
| 6,827,713 | B2 | 12/2004 | Bek et al. | |
| 2002/0028979 | A1 | 3/2002 | Silverman et al. | |
| 2002/0072738 | A1 | 6/2002 | Edwards et al. | |
| 2002/0082670 | A1 | 6/2002 | Utley et al. | |
| 2002/0115992 | A1 | 8/2002 | Utley et al. | |
| 2002/0139379 | A1 * | 10/2002 | Edwards et al. | 128/898 |
| 2002/0151871 | A1 | 10/2002 | Gaiser et al. | |
| 2002/0162555 | A1 | 11/2002 | West et al. | |
| 2002/0183735 | A1 * | 12/2002 | Edwards et al. | 606/32 |
| 2003/0023287 | A1 * | 1/2003 | Edwards et al. | 607/101 |
| 2003/0144708 | A1 | 7/2003 | Starkebaum | |
| 2003/0153905 | A1 * | 8/2003 | Edwards et al. | 606/41 |
| 2004/0089313 | A1 | 5/2004 | Utley et al. | |

FOREIGN PATENT DOCUMENTS

| | | |
|---|---|---|
| EP | 0 571 938 A2 | 12/1993 |
| WO | WO 00/69376 * | 11/2000 |
| WO | WO 02/11696 | 2/2002 |
| WO | WO 02/13854 | 2/2002 |
| WO | WO 02/053040 | 7/2002 |

* cited by examiner

SYSTEMS AND METHODS FOR TREATING OBESITY AND OTHER GASTROINTESTINAL CONDITIONS

RELATED APPLICATIONS

This application is a continuation-in-part of U.S. patent application Ser. No. 10/155,294, filed May 24, 2002, now U.S. Pat No. 6,712,074, which is a continuation of U.S. patent application Ser No. 09/304,750, filed May 4, 1999, now U.S. Pat. No. 6,402,744, which is a continuation-in-part of U.S. patent application Ser. No. 09/026,296, filed Feb. 19, 1998, now U.S. Pat. No. 6,009,877, which are each incorporated herein by reference. This application is also a continuation-in-part of U.S. patent application Ser. No. 10/156,505, filed May 28, 2002, entitled "Method to Treat Gastric Reflux via the Detection and Ablation of Gastro-Esophageal Nerves and Receptors," which is a continuation of U.S. Pat application Ser. No. 09/410,448, filed Oct. 1, 1999 now U.S. Pat. No. 6,405,732.

FIELD OF THE INVENTION

In a general sense, the invention is directed to systems and methods for treating interior tissue regions of the body. More specifically, the invention is directed to systems and methods for treating tissue in and around the stomach, including the cardia and pyloric sphincter.

BACKGROUND OF THE INVENTION

A. Obesity

It is estimated that there are over 300 million obese adult individuals worldwide. Obesity is defined as having a body weight that is 20 to 25 percent over the recommended body weight, taking into account a person's particular age, height, and sex. Usually, obesity results from eating too much and exercising too little—in other words, consuming more calories than one burns. Only a small percentage of obese individuals are obese due to a metabolic disorder.

Obesity affects virtually all age and socio-economic groups. Obesity has a multitude of physical and mental health consequences. Obese individuals are at increased risk for physical ailments such as high blood pressure, type 2 (non-insulin dependent) diabetes, coronary heart disease, osteoarthritis, gout, and certain types of cancer such as endometrial, prostate, colon and post-menopausal breast cancer. In addition to physical ailments, psychological disorders such as depression, low self-esteem, eating disorders, and distorted body image may occur in obese individuals.

The social consequences of being obese are significant. It is not uncommon for obese individuals to encounter discrimination in the job market, at school, and in social situations. Obesity can subject one to personal ridicule as well as limitations on recreational activities and clothing choices. From an increased risk of premature death to serious chronic conditions that reduce the overall quality of life, obesity is a major problem for those affected by it.

The common thread in obesity is that of a repeated imbalance in the amount of calories taken in versus the amount of energy expended. A small percentage of obese individuals ingest few calories yet maintain excess body mass because of low energy expenditure. However, more commonly, an obese person ingests a large amount of calories which sustain or increase body mass.

Why individuals overeat and become obese is a multi-faceted problem. The problem includes psychological, social, and physical components. A person may overeat in response to negative emotions such as boredom, sadness, or anger. Alternatively, a person may lack an understanding of the association between eating large quantities of energy-dense foods and weight gain and obesity. More commonly, individuals overeat in Western cultures due to hunger, social situations, and continuous access to food sources.

The term hunger describes a wide range of perceptions of an individual's drive to obtain and ingest food sources. The components of hunger include psychological drives such as eating for pleasure, and eating while socializing. The physical drives include low blood sugar, dehydration, or high levels of physical activity. The drive to overeat may be closely related to self-control issues; aberrant signals telling the individual to eat; lack of fully understanding the association between overeating and obesity; and many other possibilities.

The physical and psychological processes leading to hunger and eating are intimately intertwined. The stomach and duodenum, discussed further herein, communicate with the brain via nerve attachments as well as by hormones secreted into the bloodstream. Each structure facilitates the signals that may lead to the individual's perception of the need to eat. An example of this is "stomach growling," which is a phase indicating that a certain amount of time has passed since the last meal. A person typically interprets this activity as hunger.

The opposite of hunger is satiety. Satiety is the feeling of abdominal fullness that occurs after eating a meal. A person is said to be sated if he or she feels fully satisfied after eating.

Because of the serious medical and social complications that result from obesity, a variety of treatments are commonly employed. Treatment methods are based on a variety of factors, such as the level of obesity, the person's overall health, and the person's motivation to loss weight.

Treatment may include diet modification, exercise, behavior modification, weight-loss drugs (e.g., dexfenfluramine, sibutramine, orlistat). In serve cases, where obesity threatens the individual's life, gastrointestinal surgery may be performed. Traditional surgical techniques typically focus on making the stomach pouch smaller, such as stomach stapling, gastric bypass, or implanting an inflatable band around the upper part of the stomach. Most commonly, a multi-faceted approached utilizing a combination of these factors is employed.

B. Gastroesophageal Reflux Disease

Gastrointestinal reflux disease (GERD) is an inflammation of the esophagus resulting from regurgitation of gastric contents into the esophagus. In symptomatic people, reflux is related to an incompetent lower esophageal sphincter (LES), which is a band of muscle fibers that closes off the esophagus from the stomach. Acidic or alkaline gastric contents return to the esophagus through the LES and causes symptoms.

GERD is believed to be caused by a combination of conditions that increase the presence of acid reflux in the esophagus. These conditions include transient LES relaxation, decreased LES resting tone, impaired esophageal clearance, delayed gastric emptying, decreased salivation, and impaired tissue resistance. Since the resting tone of the lower esophageal sphincter is maintained by both myogenic (muscular) and neurogenic (nerve) mechanisms, some believe that aberrant electrical signals in the lower esophageal sphincter or surrounding region of the stomach (called the cardia) can cause the sphincter to spontaneously relax.

The most common symptom of GERD is heartburn. Besides the discomfort of heartburn, reflux results in symptoms of esophageal inflammation, such as odynophagia (pain on swallowing) and dysphagia (difficult swallowing). The acid reflux may also cause pulmonary symptoms such as coughing, wheezing, asthma, aspiration pneumonia, and interstitial fibrosis; oral symptoms such as tooth enamel decay, gingivitis, halitosis, and waterbrash; throat symptoms such as a soreness, laryngitis, hoarseness, and a globus sensation; and earache.

Complications of GERD include esophageal erosion, esophageal ulcer, and esophageal stricture; replacement of normal esophageal epithelium with abnormal (Barrett's) epithelium; and pulmonary aspiration.

C. Barrett's Esophagus

Barrett's esophagus is a disorder in which the lining of the esophagus has cellular changes in response to irritation from gastroesophageal reflux (GERD). A small percentage of patient's with GERD develop Barrett's esophagus. The normal cells lining the esophagus, squamous cells, turn into an type of cell not usually found in humans, called specialized columner cells. The diagnosis of Barrett's esophagus is typically made by viewing the esophagus with an endoscope and obtaining a sample of esophagus tissue (esophagoscopy with biopsy).

Barrett's esophagus is believed to be caused by damage caused by GERD and/or biliary reflux, in which enzymes and bile are present in the stomach despite the control of acid. In some people, there is an abnormal bile flow backwards (re-fluxing) into the stomach. The reflux of the sticky bile causes the stomach to secrete copious amounts of acid in an attempt to neutralize the bile, which is alkaline. The excess acid causes bloating and increased pressure on the LES, which often results in GERD. Therefore, symptoms are similar to those of GERD and include heartburn and difficulty swallowing.

There is increasing evidence that reflux of bile plays a part in the pathogenesis of Barrett's esophagus. Bile injury to the gastric mucosa results in a "chemical" gastritis in which oedema and intestinal metaplasia are prominent.

Serious complications have been associated with Barrett's esophagus. These include an increased risk of esophageal dysplasia and esophageal cancer.

Traditional treatment includes general measures to control GERD, medications, and surgery previously described. In more serious cases, such as when biopsy indicates dysplasic cell changes associated with increased risk of cancer, surgical removal of a portion of the esophagus (resection of the esophagus) may be performed.

SUMMARY OF THE INVENTION

The invention provides systems and methods that treat obesity and other conditions affecting the gastrointestinal tract.

One aspect of the invention achieves a tightening of the pyloric sphincter. The tightening of the pyloric sphincter can serve single or multiple physiologic purposes. The tightening can, e.g., restrict or meter the outflow of materials from the stomach through the pyloric sphincter, to prolong a feeling of satiety after eating, and thereby reduce the incidence of overeating, which can lead to obesity and other physiologic conditions. The tightening of the pyloric sphincter can, e.g., restrict or meter the backflow of acid, enzymes, and bile or other fluids through the pyloric sphincter into the stomach, to prevent or mediate the effects occasioned by contact between these materials and the stomach and/or esophagus. The systems and methods may be used as either a primary treatment modality, or applied as a supplementary treatment before, during or after a primary intervention.

According to this aspect of the invention, the systems and methods can affect tightening of the pyloric sphincter, e.g., by ablating tissue in, at, or near the pyloric sphincter. Surface tissue can be targeted for ablation, or, alternatively, tissue can be targeted for ablation below the surface, including the submucosa, the sphincter itself, or the area surrounding the sphincter. Ablation evokes a desired tissue response, which can include, e.g., an initiation of a localized healing process including influx of white blood cells and fibroblasts, followed by deposition of collagen, and a subsequent reduction in tissue compliance and tightening. These effects will result in enhanced pyloric sphincter barrier function. The ablation can be achieved by exposure of the tissue to conductive tissue heating, ohmic tissue heating, or an ablation agent, or combinations thereof.

According to this aspect of the invention, the systems and methods can also affect tightening of the pyloric sphincter, e.g., by injection of a treatment agent that evokes a desired tissue tightening response. The treatment agent can comprise, e.g., at least one sub-type of a cytokine—which can initiate a localized healing process—and/or at least one sub-type of a vanilloid-containing compound—which can cause the interruption of afferent nerve impulses affecting the pyloric sphincter. The systems and methods can also affect tightening of the pyloric sphincter, e.g., by injection of a treatment agent that may include a tissue bulking agent. Presence of the bulking agent results in additional tissue compliance reduction and tightening to enhance sphincter barrier function.

According to this aspect of the invention, the systems and methods can also affect tightening of the pyloric sphincter, e.g., by physically urging tissue at or near the pyloric sphincter toward a closely adjacent relationship, for example, by the use of magnetic force or envelopment of tissue by a constricting belt or band.

According to this aspect of the invention, the systems and methods can affect tightening of the pyloric sphincter by the combination or different treatment modalities. For example, the systems and methods can apply energy to the tissue region to form at least one lesion in conjunction with application of a treatment agent or a physical tightening device.

Another aspect of the invention mediates the receptive relaxation of muscles of the stomach in response afferent neural signals triggered by the stretching of smooth muscle occasioned by entry of food bolus into the stomach. The mediation of this neurological event can inhibit the further relaxation and stretching of stomach muscles, particularly in the fondus, to inhibit or moderate the increase in stomach volume during eating. Restricting the capacity of the stomach during food intake prolongs a feeling of satiety during and after eating. This, in turn, serves to reduce or moderate the incidence of overeating, which can lead to obesity and other physiologic conditions. The systems and methods may be used as either a primary treatment modality, or applied as a supplementary treatment before, during or after a primary intervention.

According to this aspect of the invention, the systems and methods inhibit neurological activity by ablating tissue in, at, or near regions in the stomach populated by afferent neural receptors that trigger receptive relaxation, e.g., in the cardia. These neural receptors, when stimulated by the preliminary stretching of stomach muscle by intake of food, transmit neural signals that, by interaction with the vagus nerve, command further relaxation of stomach muscle, e.g., in the fundus, thereby conditioning the stomach to stretch and receive larger volumes of swallowed material (which is a process called receptive relaxation). Ablation of tissue in, at, or near these neural receptors evokes the formation of lesions, which interrupt transmission of the neural signals and thereby inhibit or moderate receptive relaxation. Further muscle relaxation and stretching in the stomach is thereby mediated.

Surface tissue can be targeted for ablation, or, alternatively, tissue can be targeted for ablation below the surface, including the submucosa. The ablation can be achieved by exposure of the tissue to conductive tissue heating, ohmic tissue heating, or an ablation agent, or combinations thereof.

According to this aspect of the invention, the systems and methods can also affect the interruption or moderation of the receptive relaxation response by injection of a neural treatment agent in, at, or near regions in the stomach populated by afferent neural receptors, such as the cardia. The treatment agent causes the interruption of afferent nerve impulses affecting receptive relaxation. The neural treatment agent can comprise e.g., at least one sub-type of a vanilloid-containing compound. The injection of the treatment agent can be provided with or without ablation of tissue.

Yet another aspect of the invention provides systems and methods to treat obesity by moderating expansion of the stomach during intake of food. The systems and methods comprises a magnetic source fitted to a region of the stomach. The magnetic source is sized and configured to magnetically attract material fitted to another region of the stomach. The forces of magnetic attraction moderate expansion of the stomach during intake of food.

Features and advantages of these and other aspects of the invention are set forth in the following Description and Drawings, as well as in the appended claims.

DETAILED DESCRIPTION

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

I. Anatomy of the Digestive System

Figure 1:
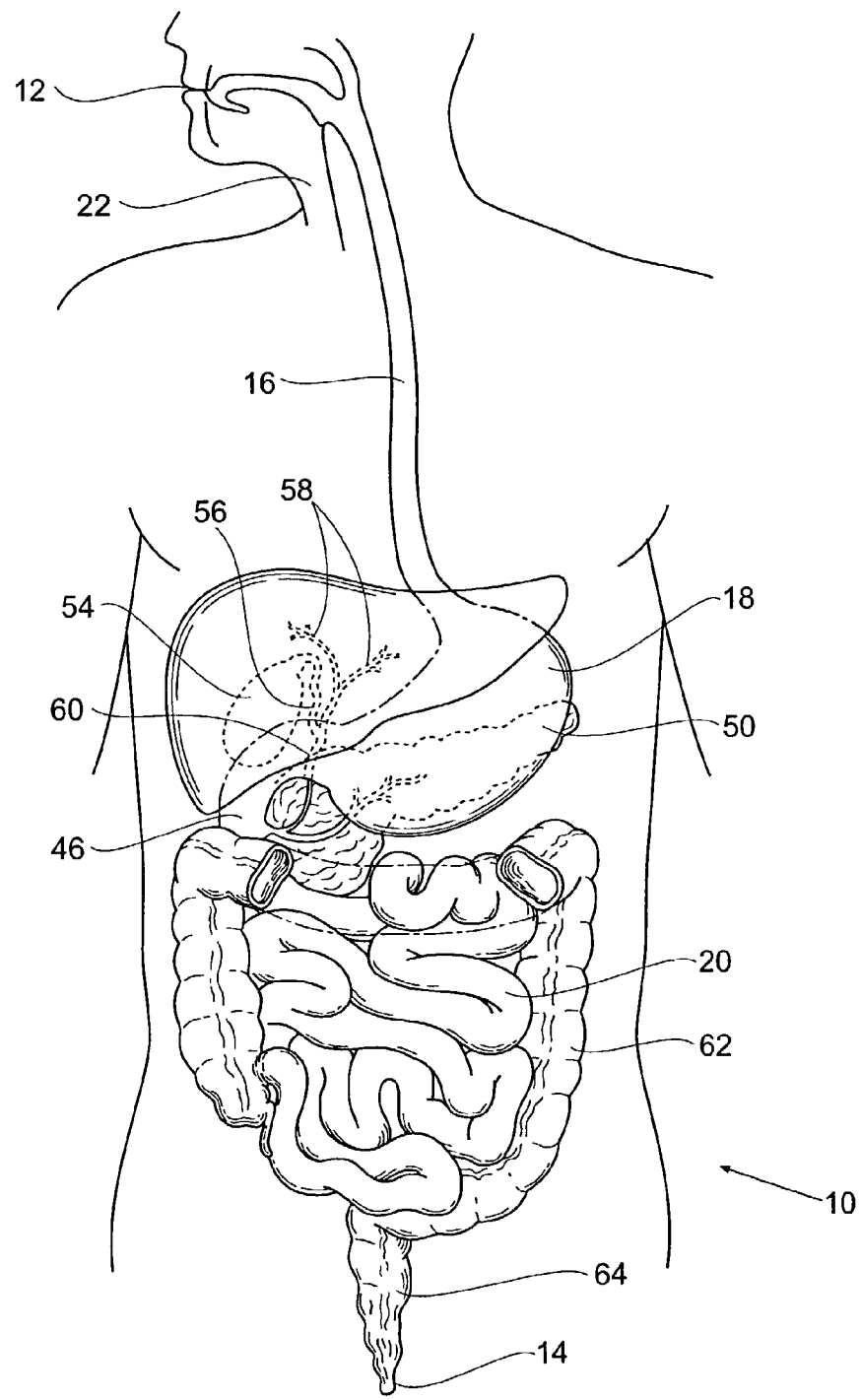
FIG. 1 is an anatomical view of the human digestive system.
Figure 2:
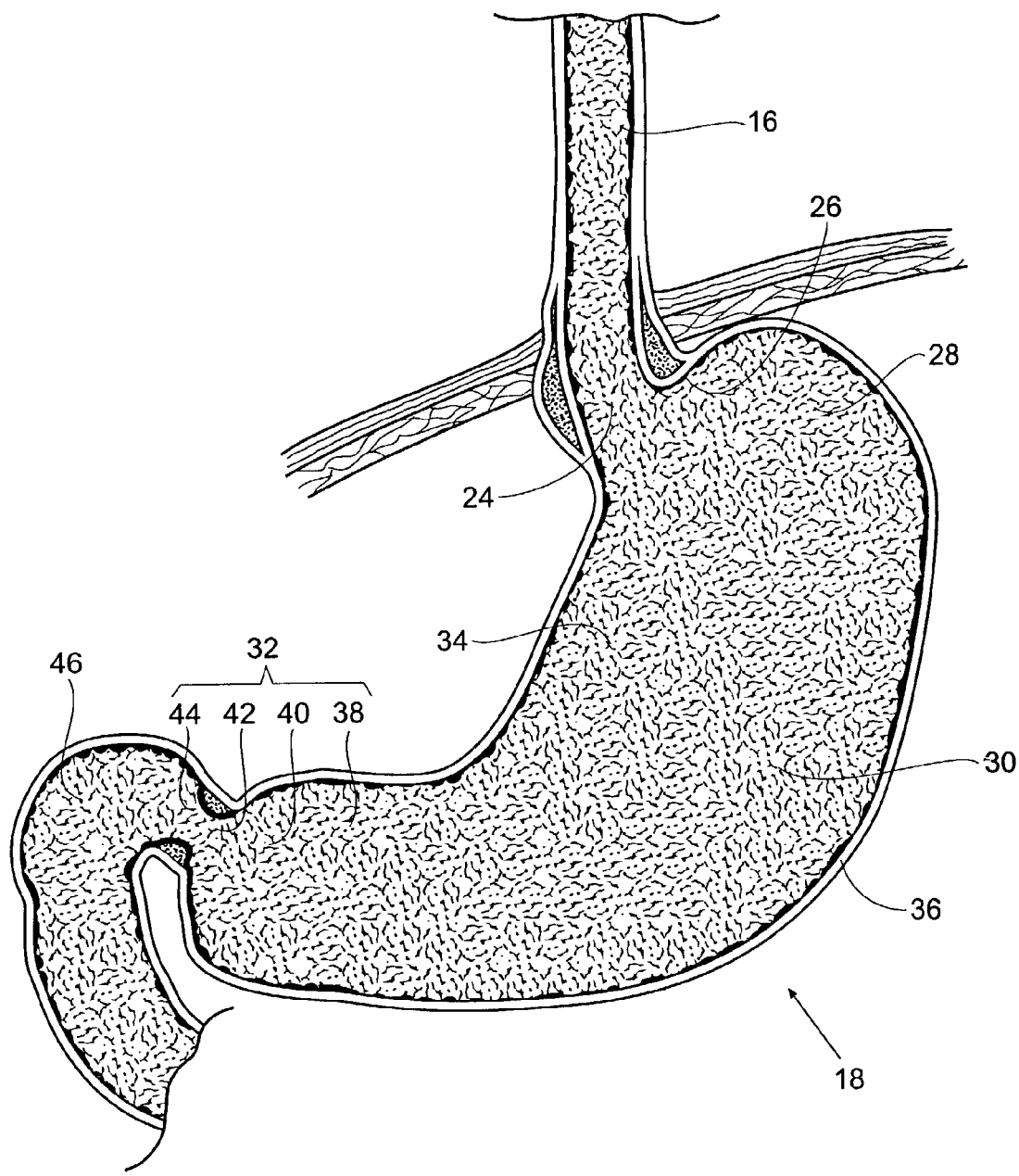
FIG. 2 is an anatomical cross-sectional view of a human stomach.

FIGS. 1 and 2 detail the human digestive system 10. The digestive system 10 consists of a series of hollow organs joined in a long, twisting tube from the mouth 12 to the anus 14. Digestion begins in the mouth 12, where food is chewed and swallowed. In order for food and drink to be changed into nourishment that the body can use, the food must be changed into smaller molecules before being absorbed into the bloodstream and transported to cells in the body. Once food is broken down into small parts, the body can use the parts to build new cells and provide energy.

Digestion includes the mixing of food, the movement of food through the digestive tract 10, and the breakdown of food from large pieces into small molecules. Food moves through the hollow organs of the digestive system 10 because such organs contain muscle that allows their walls to move. The movement of the organ walls pushes food and liquid through the digestive tract 10. This movement, of the esophagus 16, stomach 18, and small intestine 20, is called peristalsis. Peristalsis resembles ring-like contraction waves.

Food enters the digestive system 10 through the mouth 12, and is swallowed. The swallowed food is pushed into the esophagus 16. The esophagus 16 is a muscular tube that extends from the throat 22 to the stomach 18. The food then passes through the esophagus 16 and into the stomach 18.

The stomach 18 is a generally J-shaped sac that has a capacity of 1.5 liters in the average adult, but may be distended to hold up to 4 liters. Food enters the stomach 18 at its proximal end through an opening called the lower esophageal sphincter (LES) 24. The LES 24 closes the passage between the esophagus 16 and the stomach 18. However, as food approaches the LES 24, the surrounding muscles relax and allow the food to pass into the stomach 18.

The stomach 18 has four parts. The first part, the cardia 26, surrounds the LES 24. The second part is the fundus 28, a small, rounded area superior to the level of the LES 24. The fundus 28 may be dilated by swallowed air, fluid, and/or food. The third part of the stomach 18, the body 30, is the large central portion. The body 30 lies between the fundus 28 and the fourth part of the stomach 18, which is known as the pyloric part, or pyloric region 32.

In addition to the four parts of the stomach 18, there are also two curvatures. The lesser curvature 34 of the stomach 18 forms a short concave border, while the greater curvature 36 forms a long convex border of the stomach 18.

The stomach 18 thus has a proximal region, comprising the cardia 26, fundus 28, and the superior portion of the body 30. The function of the proximal region is to receive and store food for subsequent digestion. The stomach 18 also has a distal region, comprising the inferior portion of the body 30 and the pyloric part 32. The function of the distal region is to grind food.

Figure 33A:
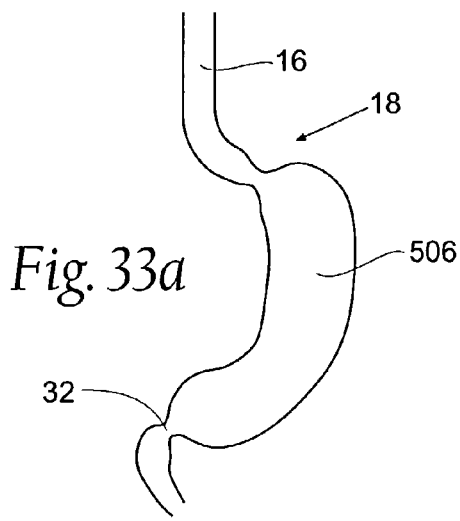
FIG. 33A is a schematic anatomic side view of a stomach before responsive relaxation occasioned by the intake of food.
Figure 33B:
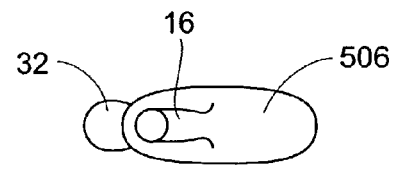
FIG. 33B is a schematic anatomic top view of the stomach shown in FIG. 33A before responsive relaxation.

After food enters the stomach 18, there are three tasks to be performed. The stomach 18 must store the swallowed food and liquid until they can be released into the small intestine 20. In order for storage to occur, as food bolus pass into the stomach, the smooth muscles in the fundus 28 of the stomach 18 relax to stretch and accept large volumes of swallowed material without an increase in interior stomach pressure. This phenomena is called receptive relaxation of the proximal stomach. FIGS. 33A/B show the stomach 18 before food intake, and FIGS. 34A/B show the stomach 18 after receptive relaxation of the proximal stomach has occurred.

Receptive relaxation is mediated by the vagus nerve, by afferent stimulation of neural receptors in the smooth stomach muscle, principally in the cardia. The smooth muscle of the stomach have the plasticity to maintain a constant tension over a wide range of muscle lengths. However, beyond a certain level of stretch, the neural receptors depolarize, sending afferent neural signals to the vagus nerve, which, in turn, sends efferent neural signals, which lead to relaxation of the smooth muscle of the fundus 28 and proximal stomach. The relaxation conditions the fundus 28 to stretch and thereby accommodate greater volumes of food.

In the second task, the stomach 18 churns the ingested nutrients. The churning breaks the ingested nutrients up into small particles. The small particles are mixed with gastric juices and produce a liquid mixture called chyme.

The third task is for the stomach 18 to slowly empty its contents into the small intestine 20, where nutrients can be absorbed.

Soon after food enters the stomach 18, peristalsis begins in specialized cells of the fundus 28 and stomach body 30. The cells are known as smooth muscle pacemaker cells. The pacemaker cells cause slow peristaltic waves to occur at a rate of three to four per minute. The slow peristaltic waves mix the contents of the stomach 18. The rhythmic contractions are known as the basic electrical rhythm, or BER, of the stomach 18. The peristaltic waves sweep downwards through the distal stomach toward the pyloric sphincter 44.

The pyloric region 32 is funnel shaped. A wide part known as the pyloric antrum 38 leads into the pyloric canal 40. The pyloric canal 40 is the narrowest part of the pyloric region 32. The pylorus 42 is found at the distal end of the pyloric region 32. The pylorus 42 is thickened and forms the pyloric sphincter at the distal end to form the pyloric sphincter 44. The pyloric sphincter 44 controls discharge of liquefied contents of the stomach 18 (i.e., chime) into the duodenum 46. The pyloric sphincter 44 is normally closed except when allowing gastric fluids to pass into the duodenum 46. The stomach 18 is continuous with the duodenum 46. The duodenum 46 is a C-shaped segment of the proximal end of the small intestine 20.

Strong peristaltic waves chop the chyme as the pylbric region 32 begins to fill. The chyme is propelled through the pyloric canal 40. With each wave, a small amount of chyme is pumped through the pyloric sphincter 44. Chyme is forced past the pyloric sphincter 44 by a mechanism known as the pyloric pump. Due to the narrowness and strength of the pyloric sphincter 44, much of the chyme is returned to the pyloric region 32. The returned chyme is further chopped by peristaltic waves.

Although the time that food is retained in stomach 18 varies, the stomach 18 usually empties in three to five hours. Gradually, the stomach 18 empties its contents into the duodenum 46. In the course of emptying, peristaltic waves move up the body 30 of the stomach 18. In so doing, the peristaltic waves ensure that all of the chyme is pushed into the pyloric region 32.

After the stomach 18 empties the food and juice mixture into the small intestine 48, the juices of two other digestive organs mix with the food to continue the process of digestion. One of these organs is the pancreas 50. It produces a juice that contains a wide array of enzymes to break down the carbohydrate, fat, and protein in food. Other enzymes that are active in the process come from glands in the wall of the intestine 20 or even a part of that wall.

The liver 52 produces yet another digestive juice—called bile. The bile is stored between meals in the gallbladder 54. Bile is secreted by the liver 52 and transmitted from that organ to the gallbladder 54 via the cystic duct 56 and hepatic ducts 58, until it is needed in the digestive process. The gallbladder 54, when functioning normally, empties through the bile duct 60 into the duodenum 46 to aid digestion by promoting peristalsis and absorption, preventing putrefaction, and emulsifying fat. At mealtime, bile is squeezed out of the gallbladder 54 into the bile duct 60 to reach the intestine 20 and mix with the fat in food. The bile acids dissolve the fat into the watery contents of the intestine 20, much like detergents that dissolve grease from a frying pan. After the fat is dissolved, it is digested by enzymes from the pancreas 50 and the lining of the intestine 20.

Digested molecules of food, as well as water and minerals from the diet, are absorbed from the cavity of the upper small intestine 20. Most absorbed materials cross the mucosa into the blood and are carried off in the bloodstream to other parts of the body for storage or further chemical change. The remaining food particles advance through the small intestine 20 into the large intestine 62 and eventually the rectum 64 for elimination through the anus 14.

II. Systems and Methods for Tightening the Pyloric Sphincter or Adjoining Tissue Regions One aspect of this Specification discloses various systems and methods for tightening tissue in, at, or near sphincters and adjoining tissue regions in the body. The systems and methods are particularly well suited for tightening the pyloric sphincter 44. For this reason, the systems and methods will be described in this context. Still, it should be appreciated that the disclosed systems and methods are applicable for use in restoring compliance to or otherwise tightening other sphincter regions (e.g., the lower esophageal sphincter or the anal sphincter), as well as other interior tissue or muscle regions in general. The systems and methods that embody features of the invention are also adaptable for use with systems and surgical techniques that are not necessarily catheter based.

Tightening the pyloric sphincter 44 slows or meters the emptying of the stomach 18. It thereby provides a method for treating obesity. By slowing or metering the emptying of the stomach 18, the feeling of satiety can be prolonged during and/or after eating. Therefore, the person takes in less food less often, resulting in weight loss over time.

Tightening of the pyloric sphincter 44 can also reduce the incidence of reflux of bile into the stomach 18 through the pylorus 42. It thereby provides a method of preventing or mediating the effects caused by the contact of bile with tissue lining the stomach 18 and/or esophagus 16, e.g., heartburn, GERD, and Barrett's esophagus.

Various treatment modalities can be used to affect tightening of the pyloric sphincter 44. Several representative modalities will be described.

A. The Tissue Treatment Devices

Figure 3:
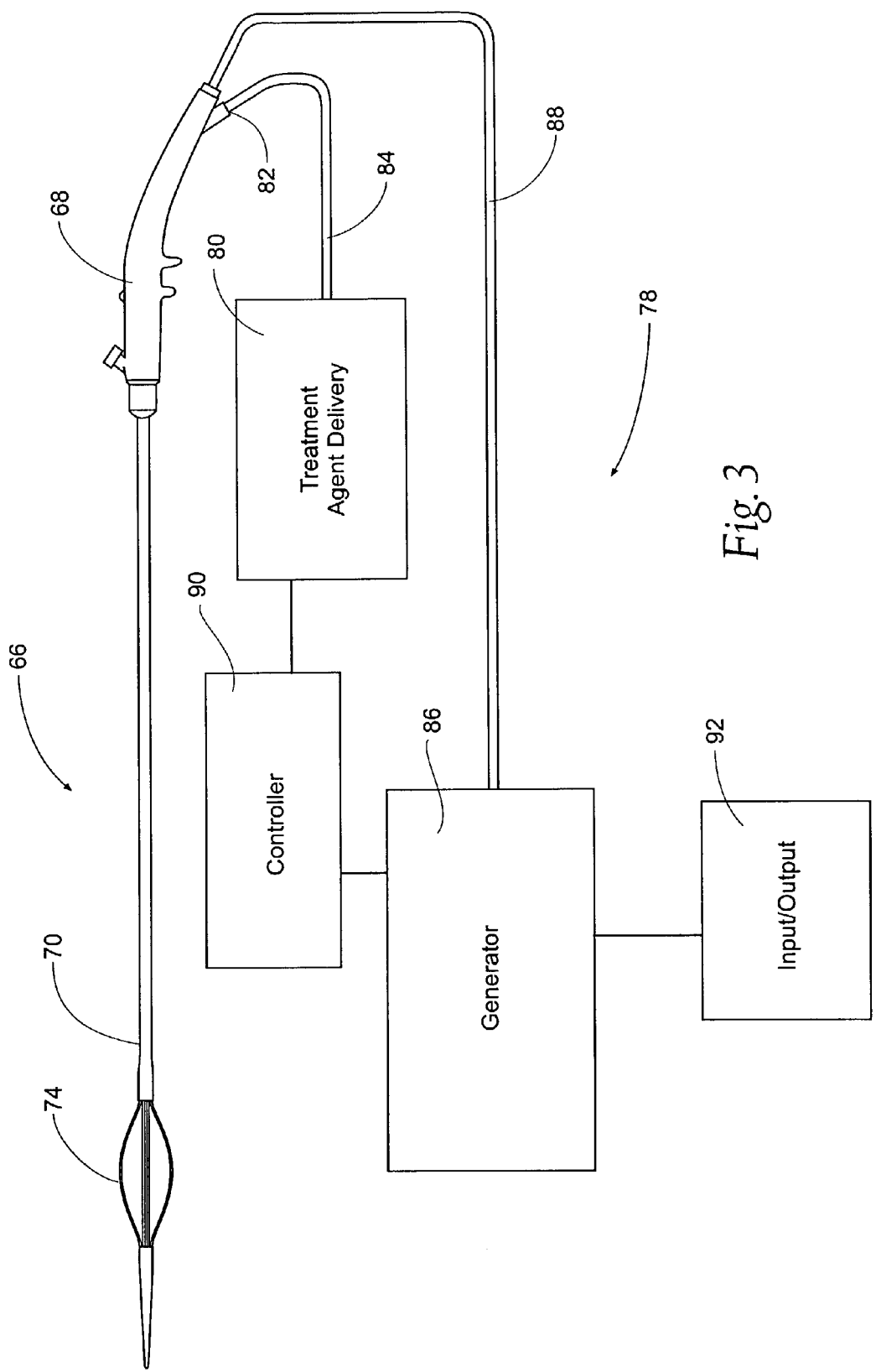
FIG. 3 is a schematic view of a treatment delivery system for treating the tissue regions of the stomach.

A tissue treatment device 66 is shown in FIG. 3 that is well suited for tightening the pyloric sphincter 44. The device 66 includes a handle 68 made, e.g., from molded plastic. The handle 68 carries a flexible catheter tube 70. The catheter tube 70 can be constructed, for example, using standard flexible, medical grade plastic materials, like vinyl, nylon, poly(ethylene), ionomer, poly(urethane), poly(amide), and poly(ethylene terephthalate). The handle 68 is sized to be conveniently held by a physician, to introduce the catheter tube 70 into the region of the pyloric sphincter 44. The catheter tube 70 may be deployed with or without the use of a guide wire 72 (see also FIG. 12).

The catheter tube 70 carries on its distal end an operative element 74.

Figure 4A:
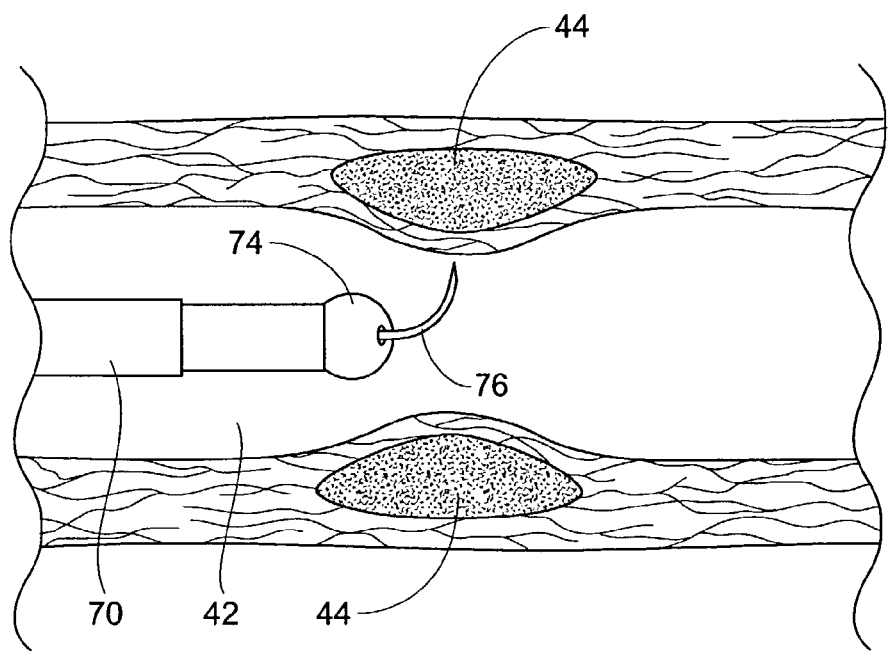
FIGS. 4A and 4B are schematic views of a system for treating a tissue region in the stomach that includes a treatment device with a tissue piercing member, FIG. 4A showing the treatment device deployed in a pyloric sphincter tissue region and FIG. 4B showing the treatment device piercing the tissue region to inject a treatment agent into the sphincter and/or ablate the tissue region, for the purpose of enhancing sphincter barrier function.
Figure 4B:
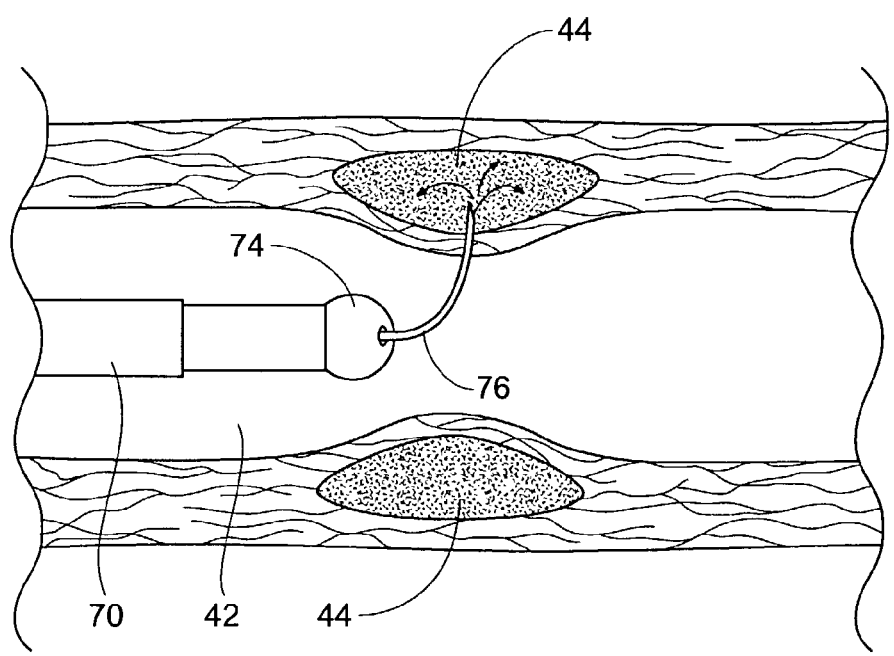
Figure 5A:
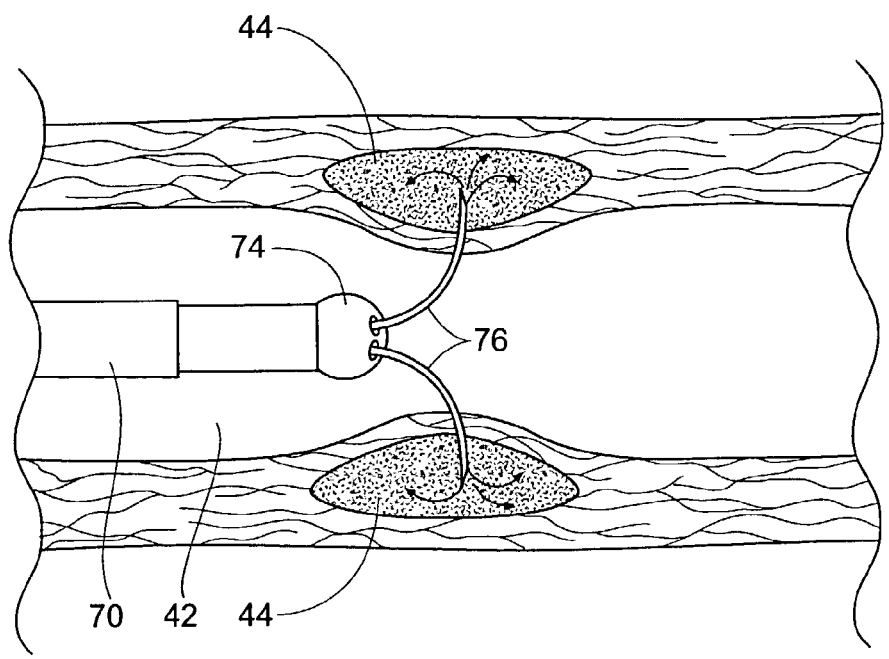
FIGS. 5A and 5B are schematic views of a system for treating a tissue region in the stomach that includes a treatment device with multiple tissue piercing members, FIG. 5A showing the treatment device deployed in a pyloric sphincter tissue region and FIG. 5B showing the treatment device piercing the tissue region to inject a treatment agent into the sphincter and/or ablate the tissue region, for the purpose of enhancing sphincter barrier function.
Figure 5B:
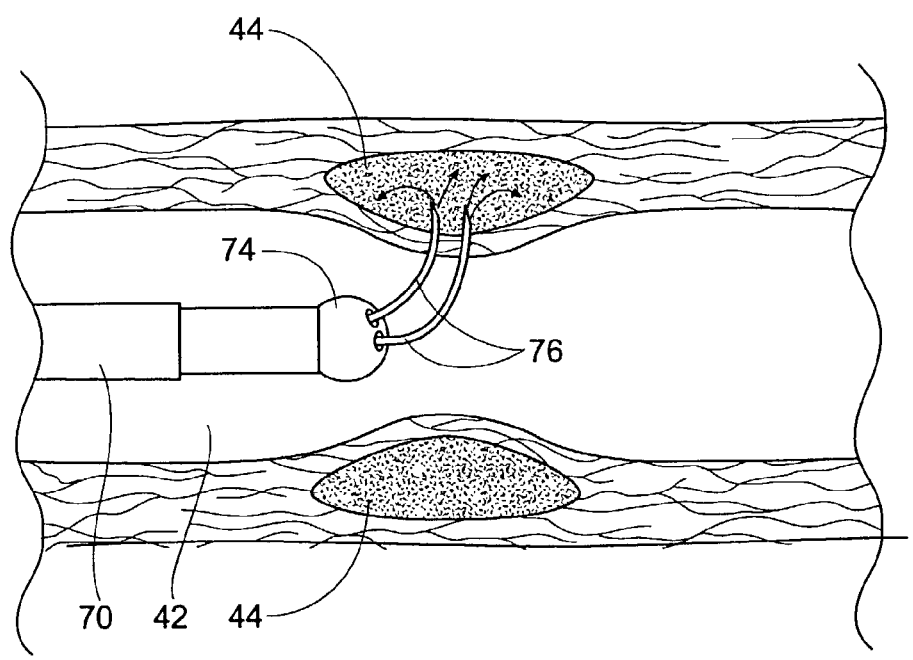

The operative element 74 includes one or more tissue piercing members 76. As FIG. 4A shows, a single tissue piercing member 76 may be used. Extension of the member 76 causes the member to pierce the adjoining tissue, as seen in FIG. 4B. Alternatively, as FIGS. 5A and 5B show, the operative element 74 can carry multiple tissue piercing members 76 in various configurations. Desirably, as will be described in greater detail later, the multiple tissue piercing members 76 are arranged in a spaced-apart array.

In one treatment modality, the operative element 74 serves to apply ablation energy in a selective fashion through the tissue piercing members 76 to tissue at, in, or near the pyloric sphincter 44. The application of ablation energy creates one or more lesions, or a prescribed pattern of lesions, below the mucosal surface. The formation of lesions by the selective application of energy incites a wound event. Natural healing of lesions tightens the targeted adjoining tissue. The healing processes results in a contraction of tissue about the lesion, to decrease its volume or otherwise alter its biomechanical properties. The healing processes naturally tighten the smooth muscle tissue within the pylorus 42. These effects will result in enhanced pyloric sphincter 44 barrier function.

The formation of lesions can be conducted by itself or in combination with the application of a treatment agent. The operative element 74 can be configured to apply the treatment agent in various ways. For example, the operative element 74 can apply the treatment agent directly to mucosal tissue overlying the sphincter 44. Alternatively, the operative element 74 can apply the treatment agent extrinsically to the sphincter 44 through mucosal tissue overlying the sphincter 44. Still alternatively, the operative element 74 can inject the treatment agent through the tissue piercing elements 76 into the sphincter 44, as represented by arrows in FIGS. 4B and 5A/B. The joint physiologic effects of lesion formation and the application of a treatment agent can interact to achieve the desired physiologic result.

For example, the treatment agent can be selected from a class of agents that lead to a physical tightening of the pyloric sphincter 44, for example, a cytokine subtype or a tissue bulking agent.

The term "cytokine subtype" as used herein means any polypeptide that affects the functions of other cells, and is a molecule which modulates interactions between cells in the immune or inflammatory response. A cytokine subtype includes, but is not limited to monokines and lymphokines regardless of which cells produce them. The cytokine-containing treatment agent can injected into the sphincter muscle, or applied extrinsically to the outside of the sphincter 44. Cytokines can serve to initiate the process of healing within the local region. This process includes, but is not limited to, influx of white blood cells and macrophages, stimulation of fibroblast and smooth muscle division and collagen secretion, new blood vessel growth, wound contraction and tightening, maturation of the new or existing collagen framework, and reduced tissue compliance. These tissue effects could improve the barrier function of the pyloric sphincter 44. Examples of cytokine materials that can be used include commercially available Regranex, which is recombinant human PDGF-BB. The cytokine-containing agent may be applied or injected as primary therapy, or applied as a supplementary treatment before, during or after a primary intervention. The ablation energy may be used to induce a wound healing process, followed by cytokine application to facilitate more exuberant wound healing.

Examples of tissue bulking agents that can be used include collagen, dermis, cadaver allograft material, or ePTFE (expanded poly-tetrafluoroethylene) pellets. The tissue bulking treatment agent can be injected into the sphincter muscle, or applied extrinsically to the outside of the sphincter 44. The tissue bulking treatment agent may be applied or injected as primary therapy, or, or applied as a supplementary treatment before, during or after a primary intervention. Ablation energy can be applied to the injected bulking agent to change its physical characteristics, e.g., to expand or harden the bulking material, to achieve a desired effect.

As another example, the treatment agent can be selected from a class of agents that interrupt afferent nerve impulses that trigger transient sphincter relation, for example, a vanilloid compound. The term "vanilloid compound" as used herein means a compound or a mixture of compounds having a biologically active vanillyl group. Vanilloid compounds include both naturally occurring vanilloids, synthetic vanilloids, pharmaceutically acceptable salts of the vanilloid compound (whether natural or synthetic) as well as pharmaceutically acceptable derivatives and/or analogues thereof (whether natural or synthetic). Examples of natural vanilloid compounds include both the crude extracts and the purified extracts of active vanilloid compounds from: capsicum, cayenne pepper, black pepper, paprika, cinnamon, clove, mace, mustard, ginger, turmeric, papaya seed and the cactus-like plant Euphorbia resinifera. Synthetic vanilloid compounds such as synthetic capsaicin are disclosed in WO 96/40079, which is incorporated herein by reference. An example of vanilloid materials that can be used is produced by Afferon and is called RTX. The use of a vanilloid-containing treatment agent can serve to interrupt afferent impulses which trigger transient sphincter relaxations, and thereby enhance sphincter barrier function. The vanilloid-containing treatment agent can be applied to the mucosal lining or extrinsically to the outside of the sphincter 44. The vanilloid-containing treatment agent may be applied or injected as primary therapy, or applied as a supplementary treatment before, during or after a primary intervention. Ablation energy may be used to incite a wound, followed by application of the vanilloid-containing treatment agent to facilitate exuberant wound healing.

These treatment modalities, alone or in combination, can thereby enhance the barrier function of the pyloric sphincter.

As FIG. 3 shows, the treatment device 66 can operate as part of a system 78. The system 78 includes an external treatment agent delivery apparatus 80. A luer fitting 82 on the handle 68 couples to tubing 84 to connect the treatment device 66 to the treatment agent delivery apparatus 80, to delivery the treatment agent for discharge by or near the operative element 74. Alternatively, or in combination, the system 78 can include a generator 86 to supply energy to the operative element 74, if formation of lesions is desired. A cable 88 coupled to the handle 68 conveys the generated energy to the operative element 74.

In the illustrated embodiment, the generator 86 supplies radiofrequency energy, e.g., having a frequency in the range of about 400 kHz to about 10 mHz. Of course, other forms of tissue ablation energy can be applied, e.g., coherent or incoherent light; heated or cooled fluid; resistive heating; microwave; ultrasound; a tissue ablation fluid; or cryogenic fluid.

The system 78 also desirably includes a controller 90. The controller 90 is linked to the generator 86 and the treatment agent delivery apparatus 80. The controller 90, which preferably includes an onboard central processing unit, governs the power levels, cycles, and duration that the radio frequency energy is distributed to the operative element 74, to achieve and maintain power levels appropriate to achieve the desired treatment objectives. In tandem, the controller 90 can also governs the delivery of the treatment agent.

The controller 90 desirably includes an input/output (I/O) device 92. The I/O device 92 allows the physician to input control and processing variables, to enable the controller 90 to generate appropriate command signals.

Figure 6:
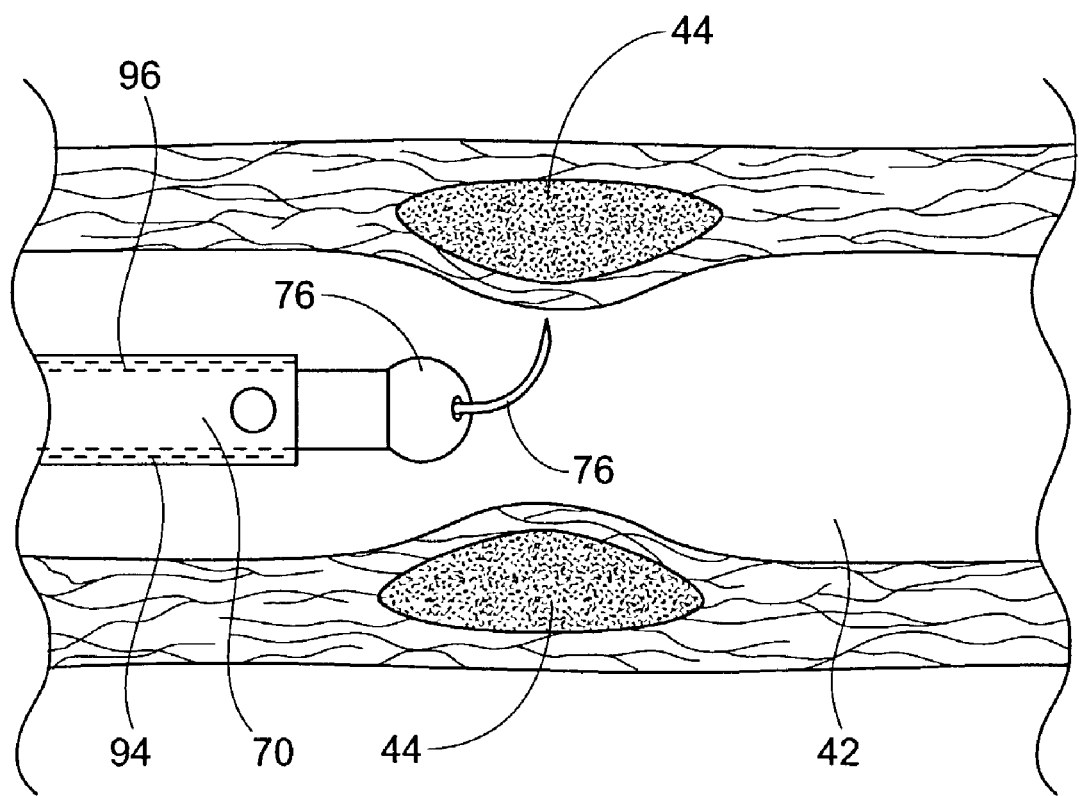
FIG. 6 is a schematic view of the tissue treatment device of a type shown in FIG. 4A being deployed in a pyloric sphincter tissue region through an endoscope.

Since the treatment site can not be directly visualized, the treatment device 66 can be introduced using an endoscope 94 having an interior lumen 96 passed down the esophagus 16 through the mouth 12, as FIG. 6 shows. In this arrangement, the catheter tube 70 is passed through the endoscope lumen 96 to the targeted site at or near the pyloric sphincter 44. A guidewire 72 may be used, if desired, to further facilitate deployment of the endoscope 94 and treatment device 66 to the targeted site.

Figure 7:
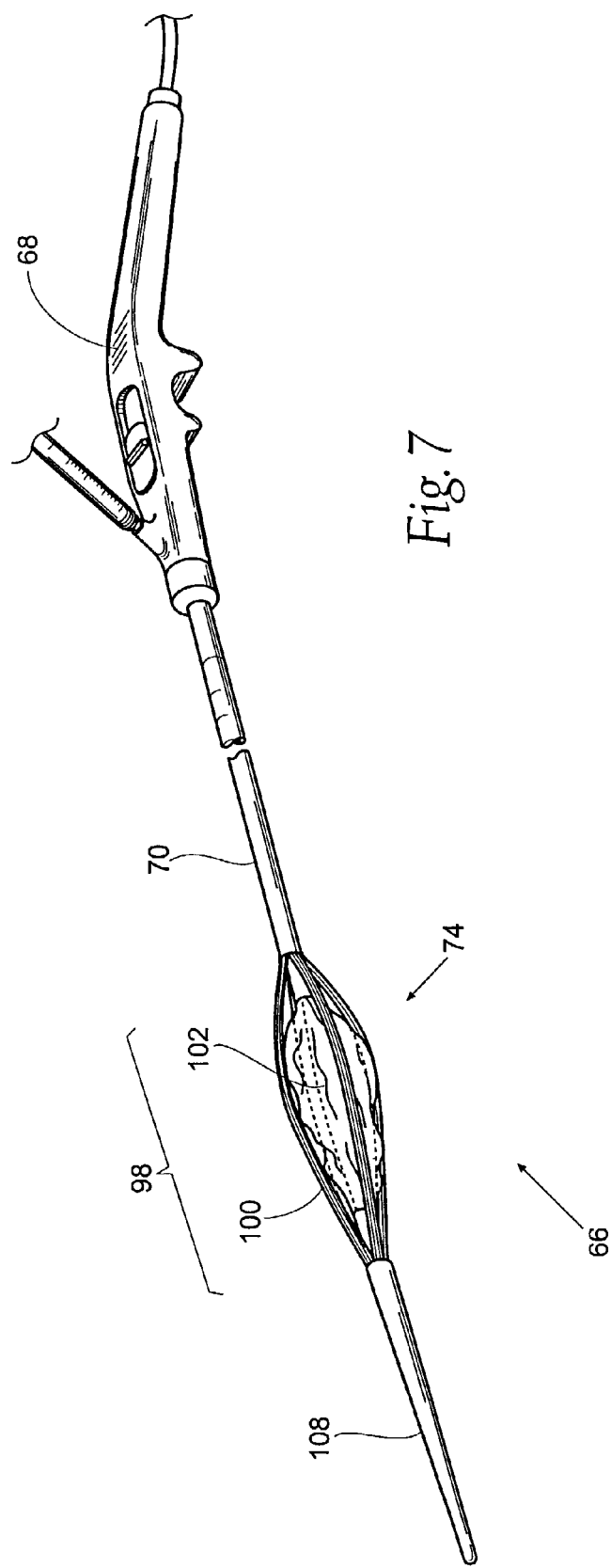
FIG. 7 is a perspective view of a treatment device for injecting a treatment agent and/or forming lesions in and around the pyloric sphincter region, with the basket element carried by the device shown in a collapsed condition for deployment to a targeted tissue region.
Figure 8:
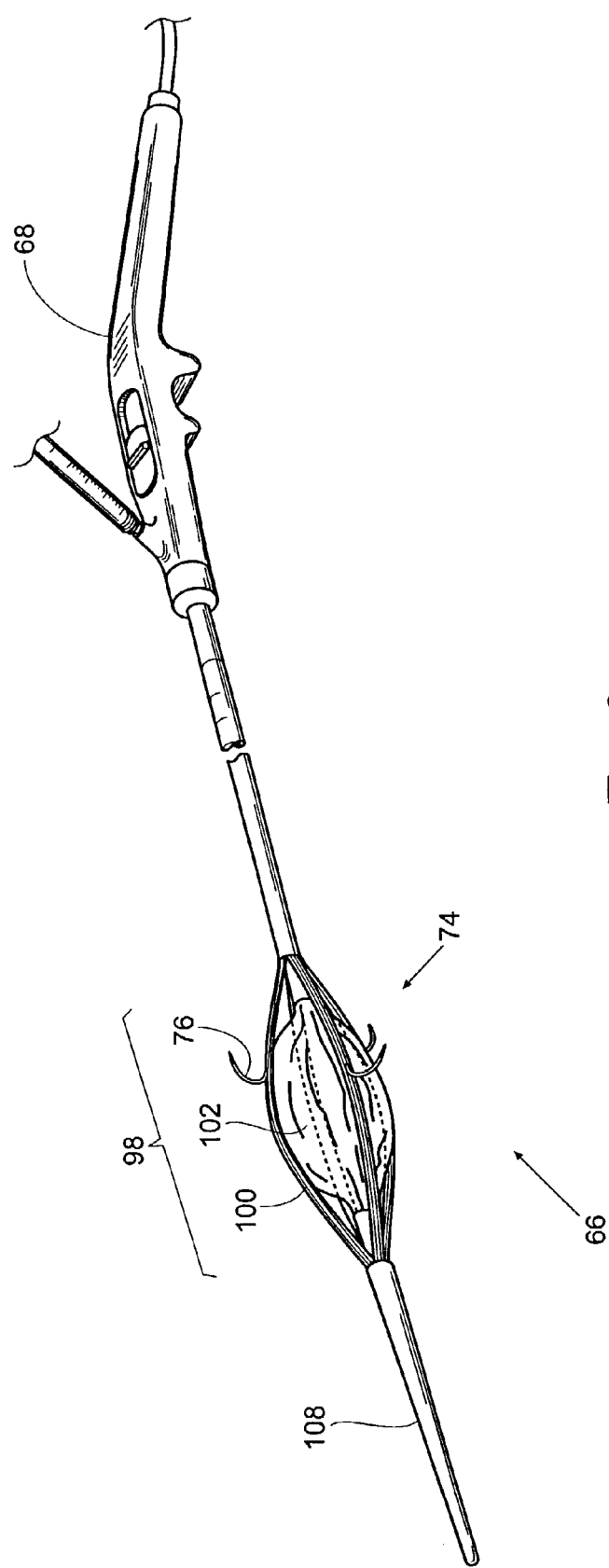
FIG. 8 is a perspective view of the treatment device shown in FIG. 7, with the basket element carried by the device shown in an expanded condition, as it would be when ready for use in a targeted tissue region.

As shown in FIG. 7, the operative element 74 can comprise an expandable structure 98. The expandable structure 98 includes an array of tubular spines 100 that form a basket that is capable of being selectively expanded and contracted. The expandable structure 98 can further comprise an inflatable body 102 (e.g., balloon) within the basket. The purpose of the inflatable body 102 is to cause the basket to expand and contract within the pylorus 42. The expanded balloon structure 102 serves to temporarily dilate the targeted tissue, thus removing some or all the folds normally present in the mucosal surface. FIG. 7 shows the expandable structure 98 in the contracted or collapsed position. FIG. 8 shows the expandable structure 98 in the expanded position.

In this arrangement, the tissue piercing elements 76 are carried within the spines 100 and are similarly capable of extension and retraction. The elements 76 are selectively movable between two positions. The first position is a retracted position, illustrated in FIG. 7, in which they are withdrawn in a spine 100. The second position is an extended position, illustrated in FIG. 8, in which they extend outward from the spine 100 through a hole in the spine 100. The tissue piercuing elements 76 serve as electrodes, which can be arranged in bipolar pairs or in a singular, spaced apart relation suitable for monopolar operation.

Figure 9:
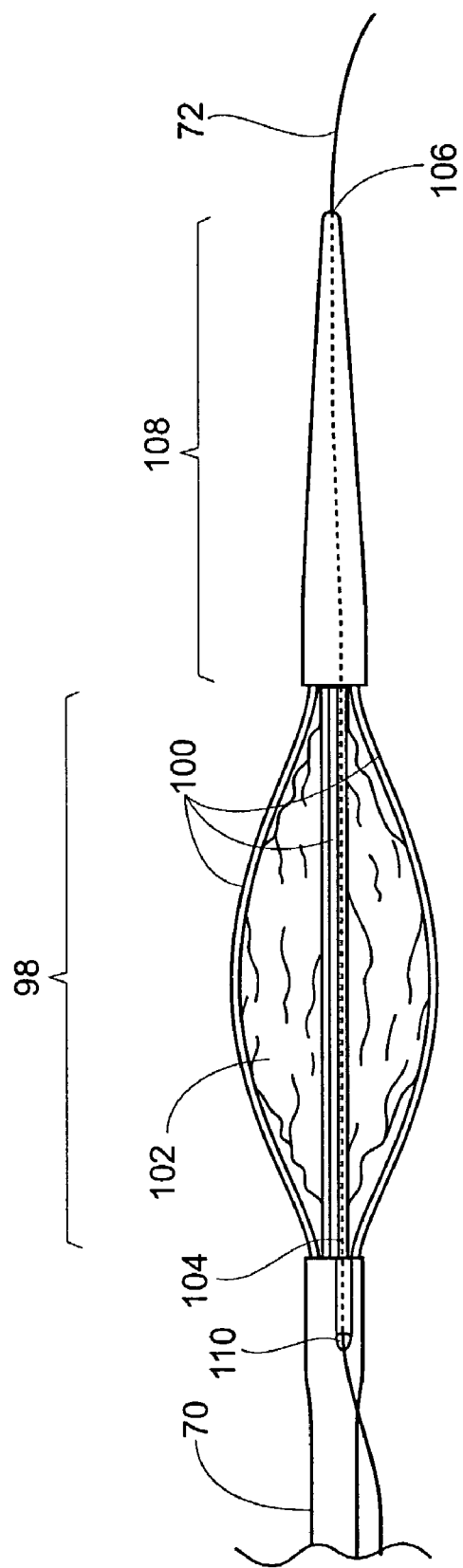
FIG. 9 is a side view of the distal end of the treatment device shown in FIG. 8, showing the passage of a guide wire to aid deployment of the device to a targeted tissue region.

A preferred embodiment is shown in FIG. 9. Here, one of the spines 100 of the expandable structure 98 provides a lumen 104 for passage of a guidewire 72. This path provides stability and support for the expandable structure 98 during passage over the guidewire 72. The lumen 104 has a distal opening 106 located beyond the distal end of the expandable structure 98. The opening 106 serves as an exit for a guidewire 72 threaded through a guide assembly 108. The lumen 104 also has a proximal opening 110 that extends proximal of the proximal end of the expandable structure 98. The proximal opening 110 rests on the exterior of the catheter tube 70 to provide for an unimpeded passage of the guidewire 72.

Figure 10:
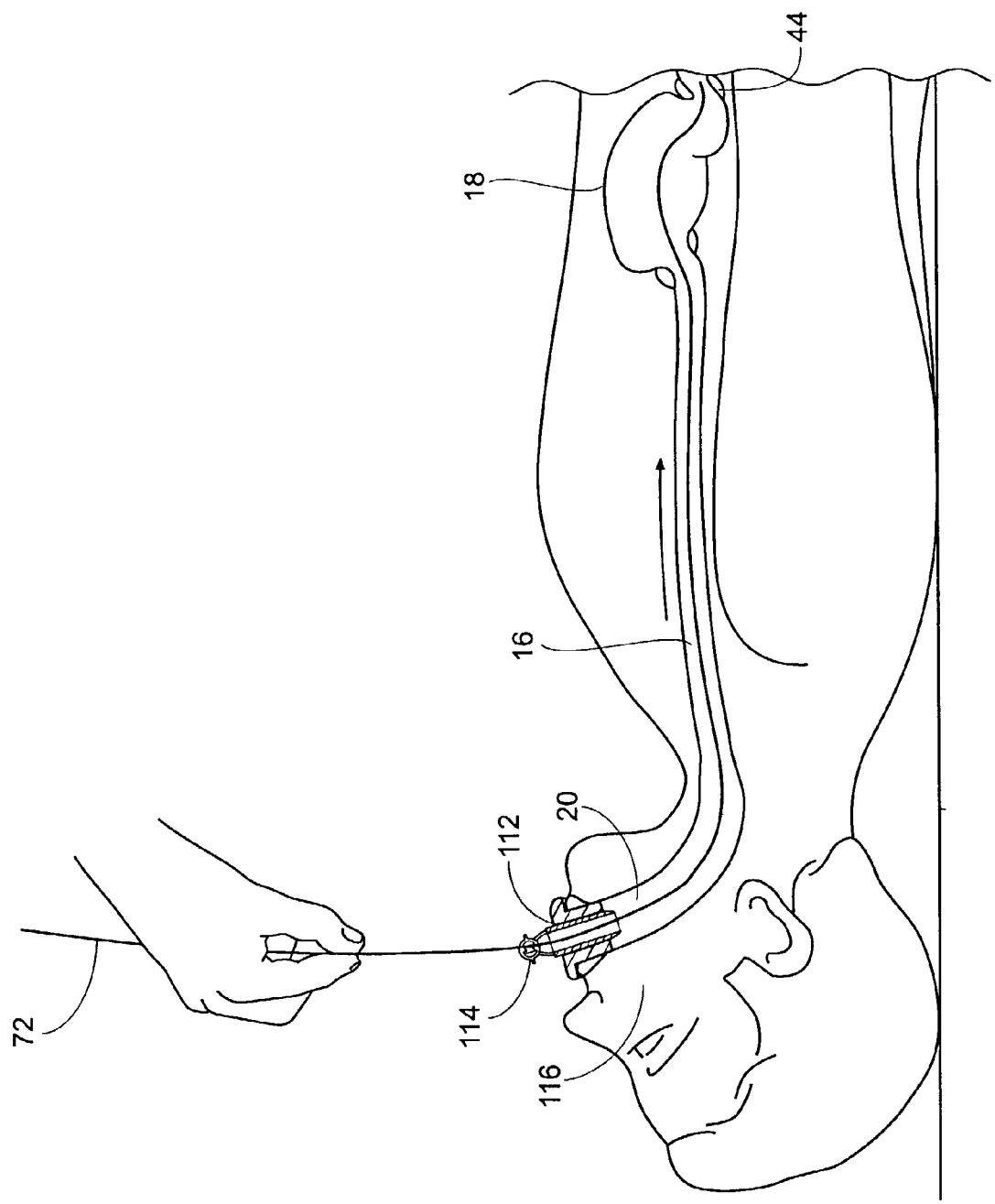
FIGS. 10 to 19 are schematic views showing the deployment of the treatment device shown in FIGS. 7 to 9 into the stomach and, in particular, the pyloric sphincter tissue region of the stomach to inject a treatment agent into the sphincter and/or ablate the tissue region, for the purpose of enhancing sphincter barrier function.

With reference to FIG. 10, to deploy the expandable structure 98, as a patient lies awake in a reclined or semi-reclined position, a bite block 112 is placed in the patient's mouth and is properly positioned. The bite block 112 is used to hold open the patient's mouth while inserting the device 66 into the individual's oral cavity. Desirably, the bite block 112 carries a gripping tool 114. The gripping tool 114 is used to hold the device 66 in a proper position. By contacting the periphery of the device 66, the gripping tool 114 maintains the device 66 in a fixed position within the bite block 112. Both the bite block 112 and the gripping tool 114 are disclosed in co-pending U.S. patent application Ser. No. 10/017,906, filed Dec. 14, 2001 and entitled "Systems and Methods Employing a Guidewire for Positioning and Stabilizing External Instruments Deployed Within the Body," and are incorporated herein by reference.

As FIG. 10 illustrates, the physician then passes the small diameter guidewire 72 through the patient's mouth 12 and pharynx 116. The guidewire 72 is directed through the esophagus 16 and into the patient's stomach 18. The distal end of the guidewire 72 is positioned at the targeted site in the pylorus 42. For purposes of treating obesity and GERD, the targeted site is the pyloric sphincter 44 and regions adjacent thereto, as best seen in FIG. 2.

Figure 11:
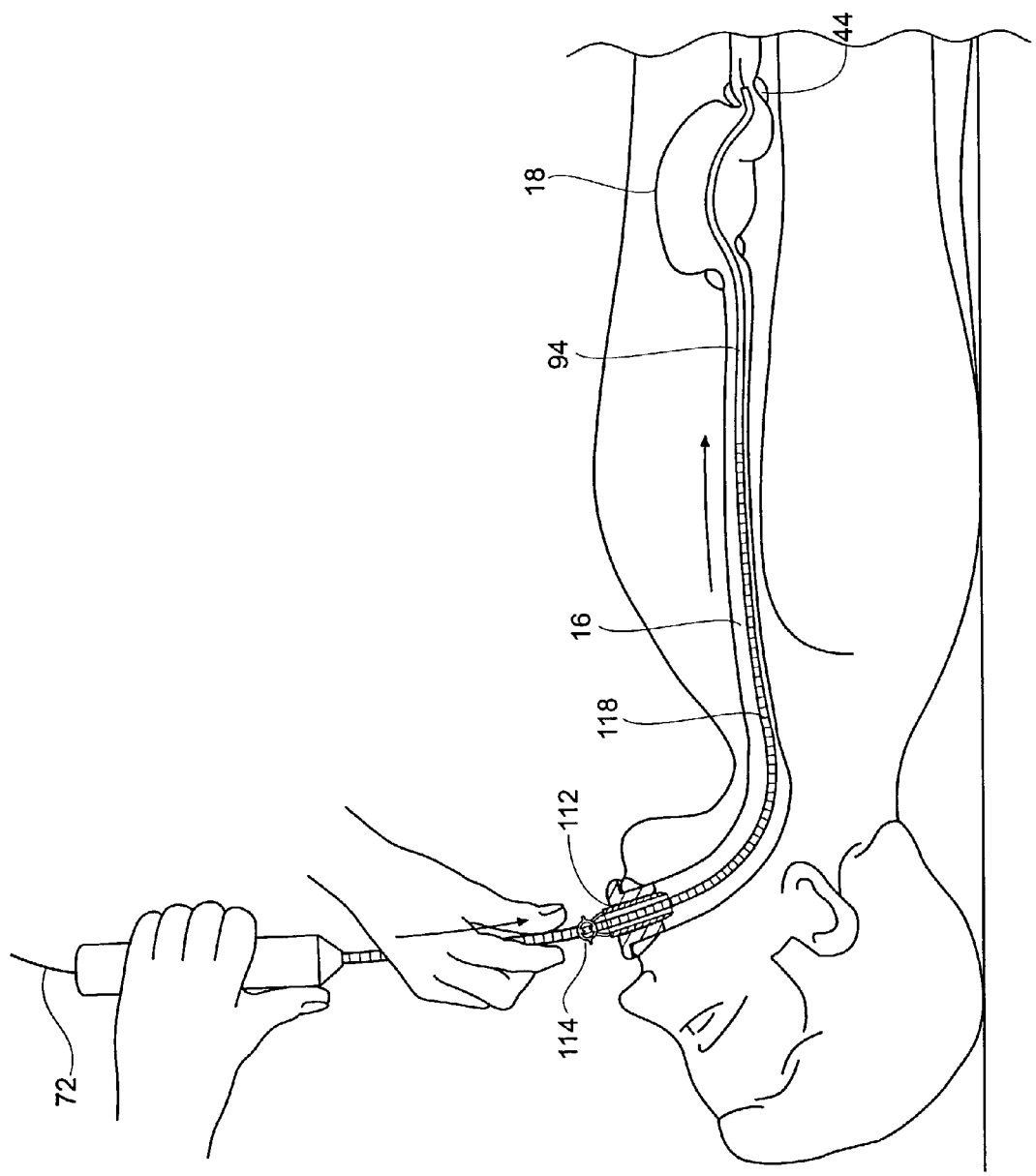

Desirably, the physician employs an endoscope 94 in conjunction with the guidewire 72 for visualizing the targeted site. Use of an endoscope 94 is shown in FIG. 11. It should be appreciated, however, that the physician may instead employ fluoroscopy for visualizing the targeted site. The endoscope 94 can be either separately employed in a side-by-side relationship with the guidewire 72, or, as shown in FIG. 11 the endoscope 94 may be introduced over the guidewire 72 itself.

The body of the endoscope 94 includes measured markings 118 along it length. The markings 118 indicate the distance between a given location along the body and the endoscope 94. Relating the alignment of the markings 118 to the bite block 112, the physician can gauge, in either relative or absolute terms, the distance between the patient's mouth 12 and the endoscope 94 in the pyloric region 32. When the physician visualizes the targeted site, e.g., the pyloric sphincter 44, with the endoscope 94, the physician records the markings 118 that align with the bite block 112 and removes the endoscope 96, leaving the guidewire 72 behind.

In the illustrated embodiment, the catheter tube 70 includes measured markings 120 along its length. The measured markings 120 indicate the distance between a given location along the catheter tube 70 and the operative element 74. The markings 120 on the catheter tube 70 correspond in spacing and scale with the measured markings 118 along the tubal body of the endoscope 94.

Figure 12:
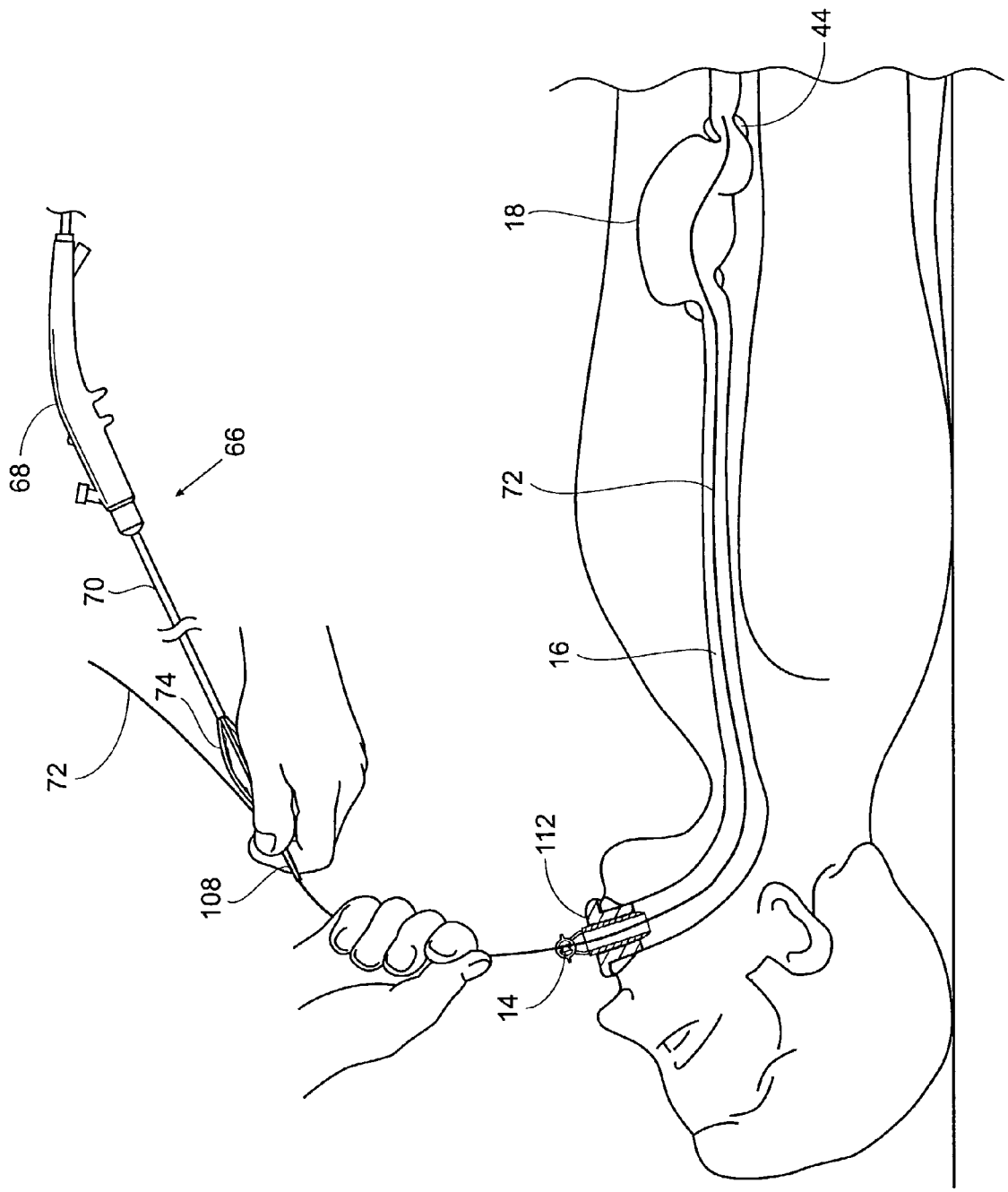
Figure 13A:
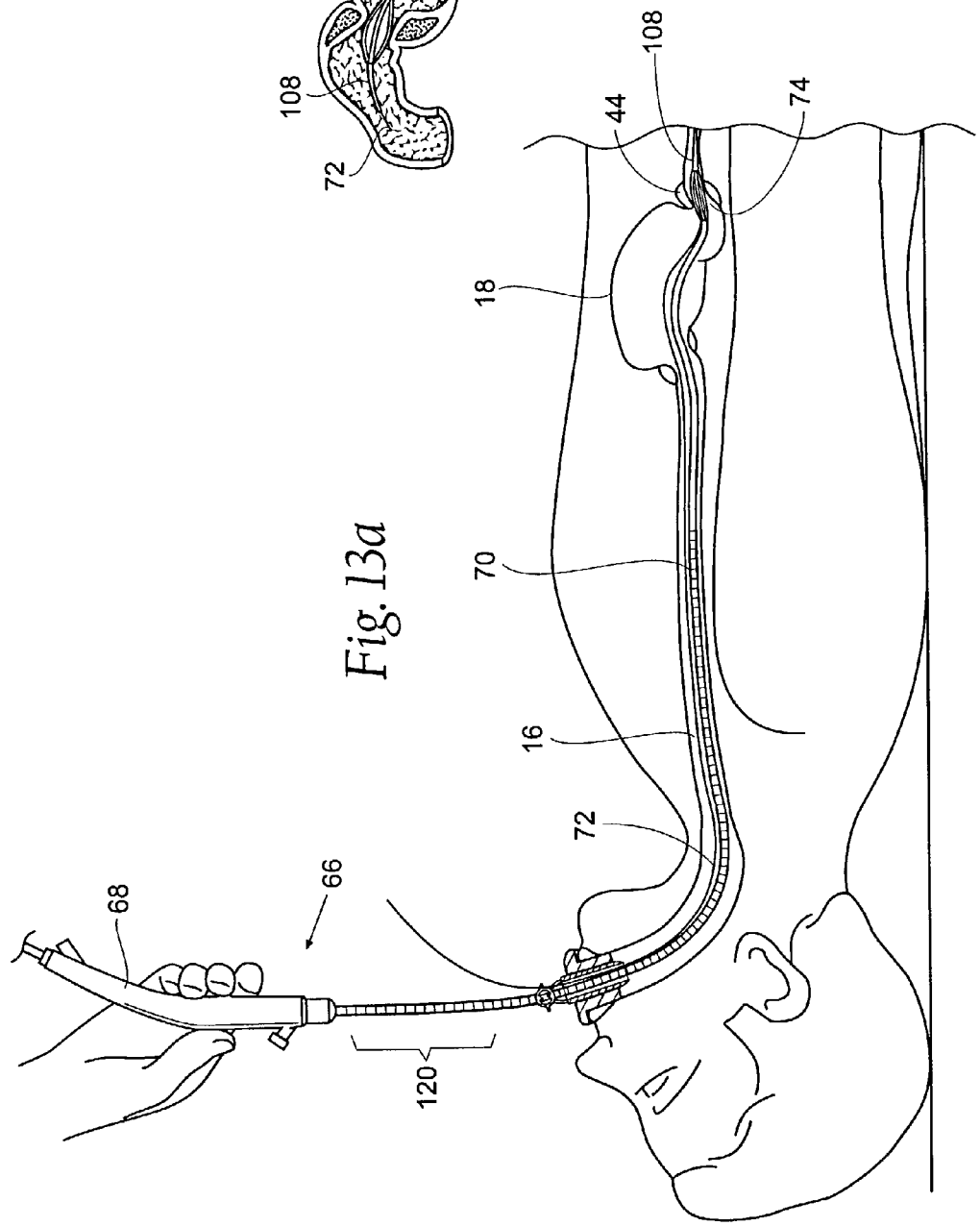
Figure 13B:
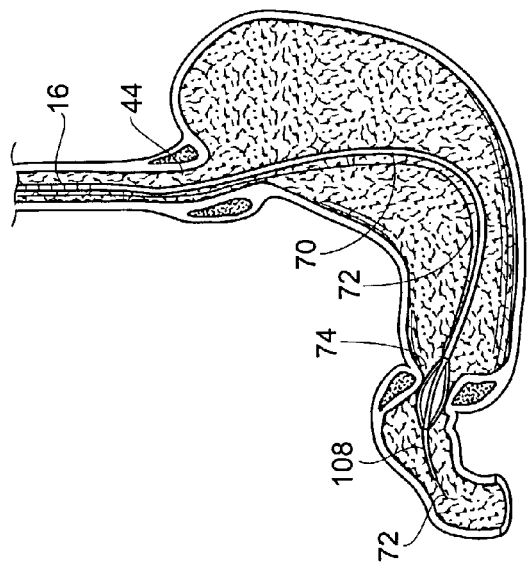

As the treatment begins, the free proximal end of the guidewire 72 is threaded through the distal opening in the guidewire lumen 104 of the expandable structure 98 such that the guidewire 72 exits the lumen 104 through the proximal opening 110, as illustrated in FIG. 12. The device 66 is then introduced over the guidewire 72 through the patient's mouth 12 and pharynx 116, to the desired position in the pyloric region 32, e.g., the pyloric sphincter 44. During passage of the device 66 over the guidewire 72, the expandable structure 98 is in a collapsed condition, and the electrodes 74 are in a retracted position. The positioning of the device 66 within the pyloric sphincter 44 is shown in FIGS. 13A and 13B.

Figure 14:
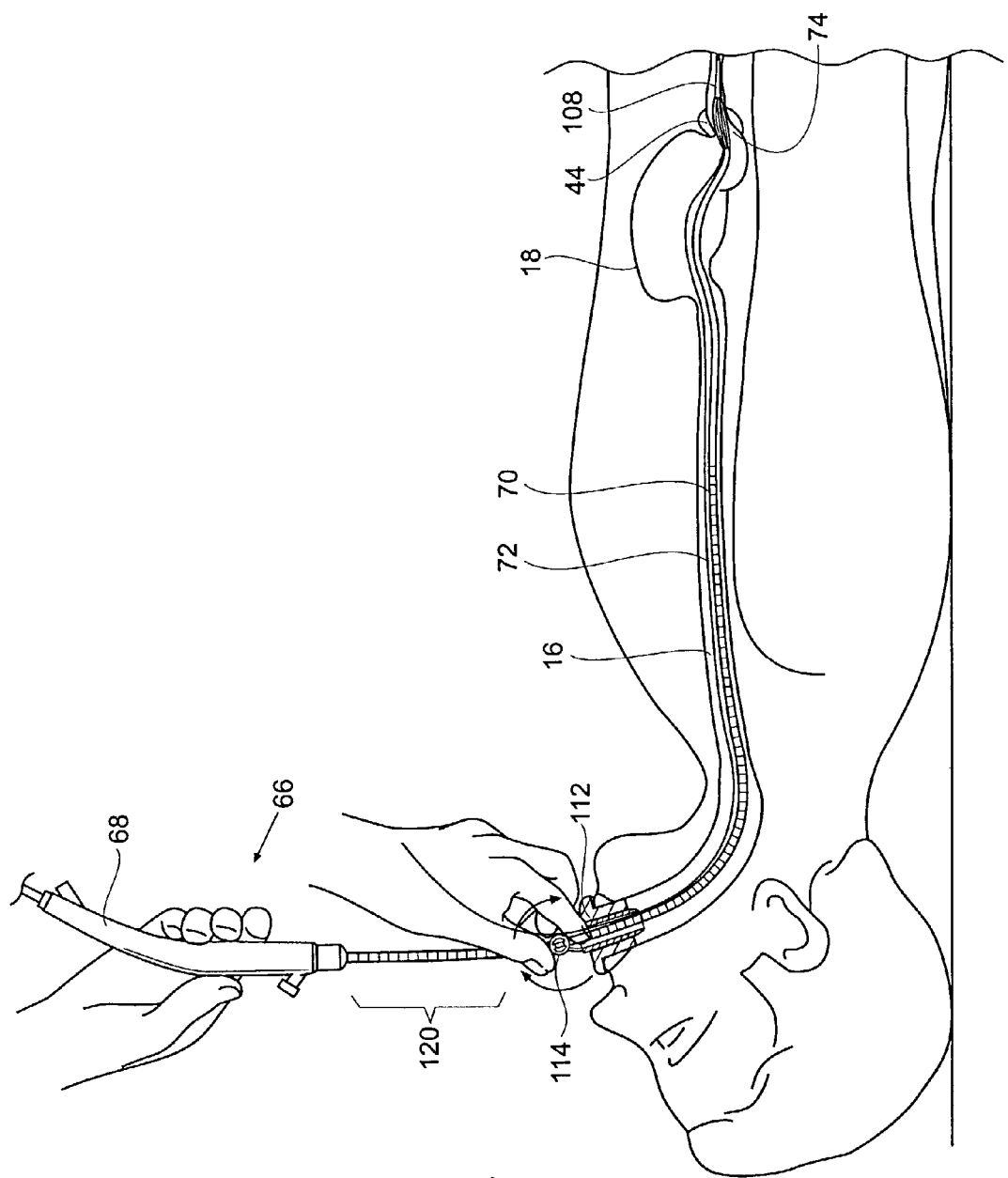

Tissue ablation is then performed. First, the device 66 is held in the desired position by closing gripping elements of the gripping tool 114, as seen in FIG. 14.

Figure 15:
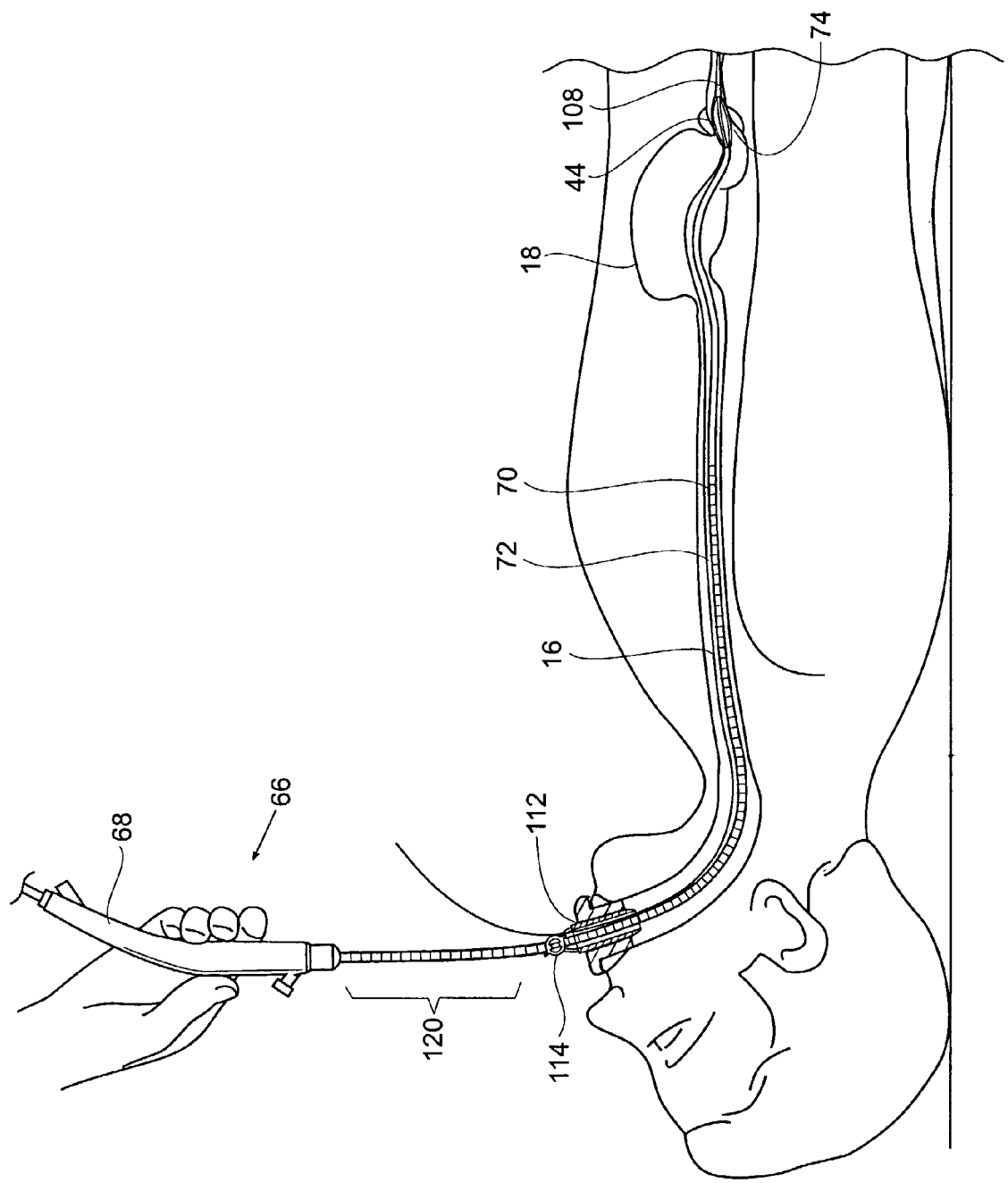

Next, as illustrated in FIG. 15, the expandable structure 98 is expanded by injecting fluid or air into the inflatable member 102, e.g., sterile water or air is injected in balloon through port in handle 68 of device 66, causing it to inflate. Inflation of the inflatable member 102 causes the expandable structure 98 to expand, making intimate contact with the mucosal surface of the pyloric sphincter 44. The expanded structure 98 serves to temporarily dilate the pyloric sphincter 44 to remove some or all of the folds normally present in the mucosal surface. The expanded structure 98 also places the spines 100 in intimate contact with the mucosal surface.

Figure 16:
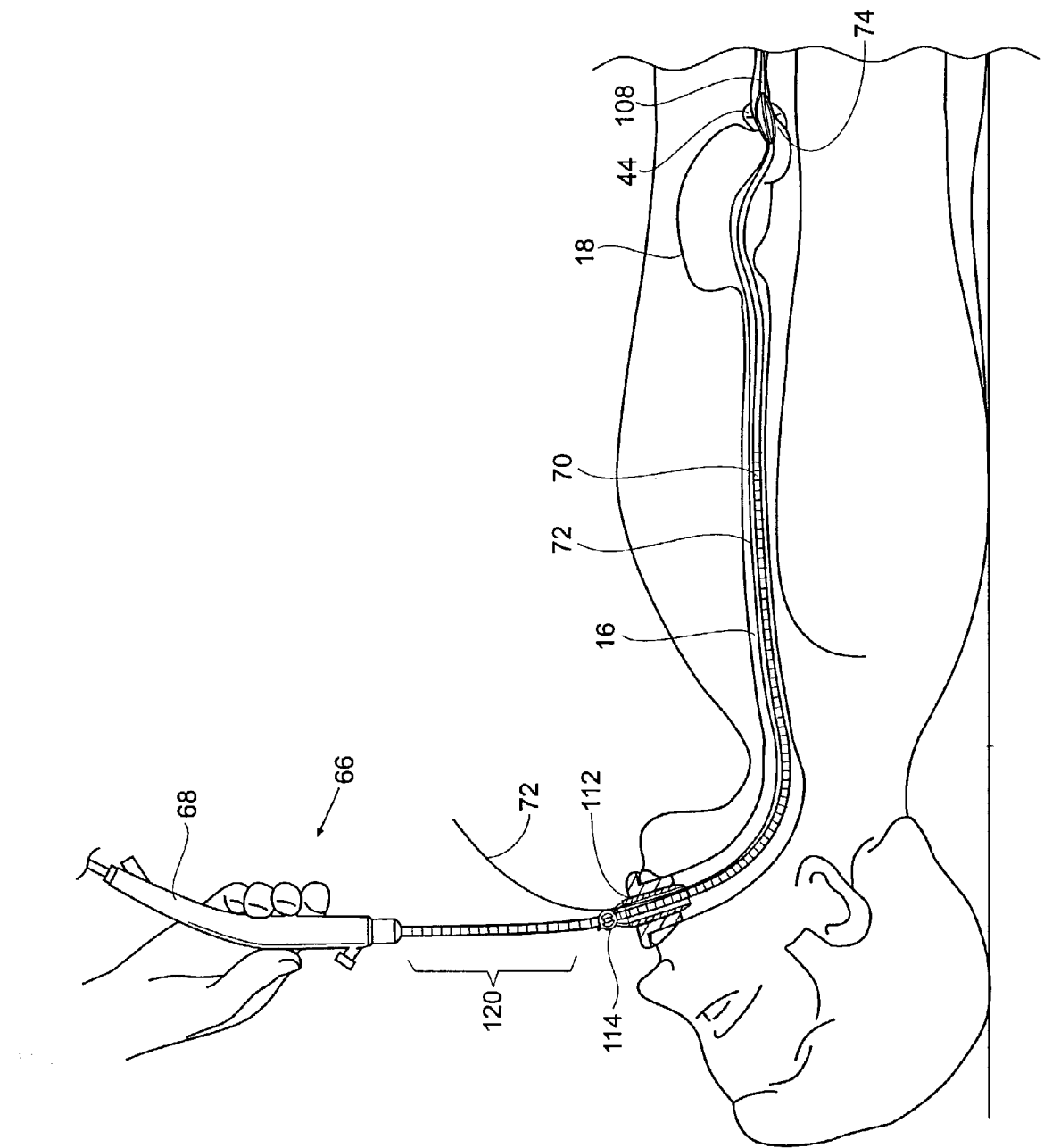

The electrodes 76 are now moved into their extended position, e.g., by operation of a push-pull lever on the handle 68 of the device 66, as illustrated in FIG. 16. The electrodes 76 pierce and pass through the mucosal tissue into the smooth muscle tissue of the pyloric sphincter 42.

Next, the physician applies energy, such as radio frequency energy for a desired period of time, e.g., approximately 400 kHz to about 10 mHz is applied for about 90 seconds. If desired, cooling liquid can be introduced during the ablation sequence (e.g., each spine 100 can include an interior lumen with a port to convey a cooling liquid such as sterile water into contact with the mucosal surface of the targeted tissue site (not shown).

The radio frequency energy ohmically heats the smooth muscle tissue. Temperature is sensed in the electrodes 32 by sensors 60 carried therein (not shown) Desirably, for a region of the pyloric sphincter 44, energy is applied to achieve tissue temperatures in the smooth muscle tissue in the range of 55° C. to 95° C. In this way, lesions can typically be created at depths ranging from one to four millimeters below the mucosal surface.

Figure 17:
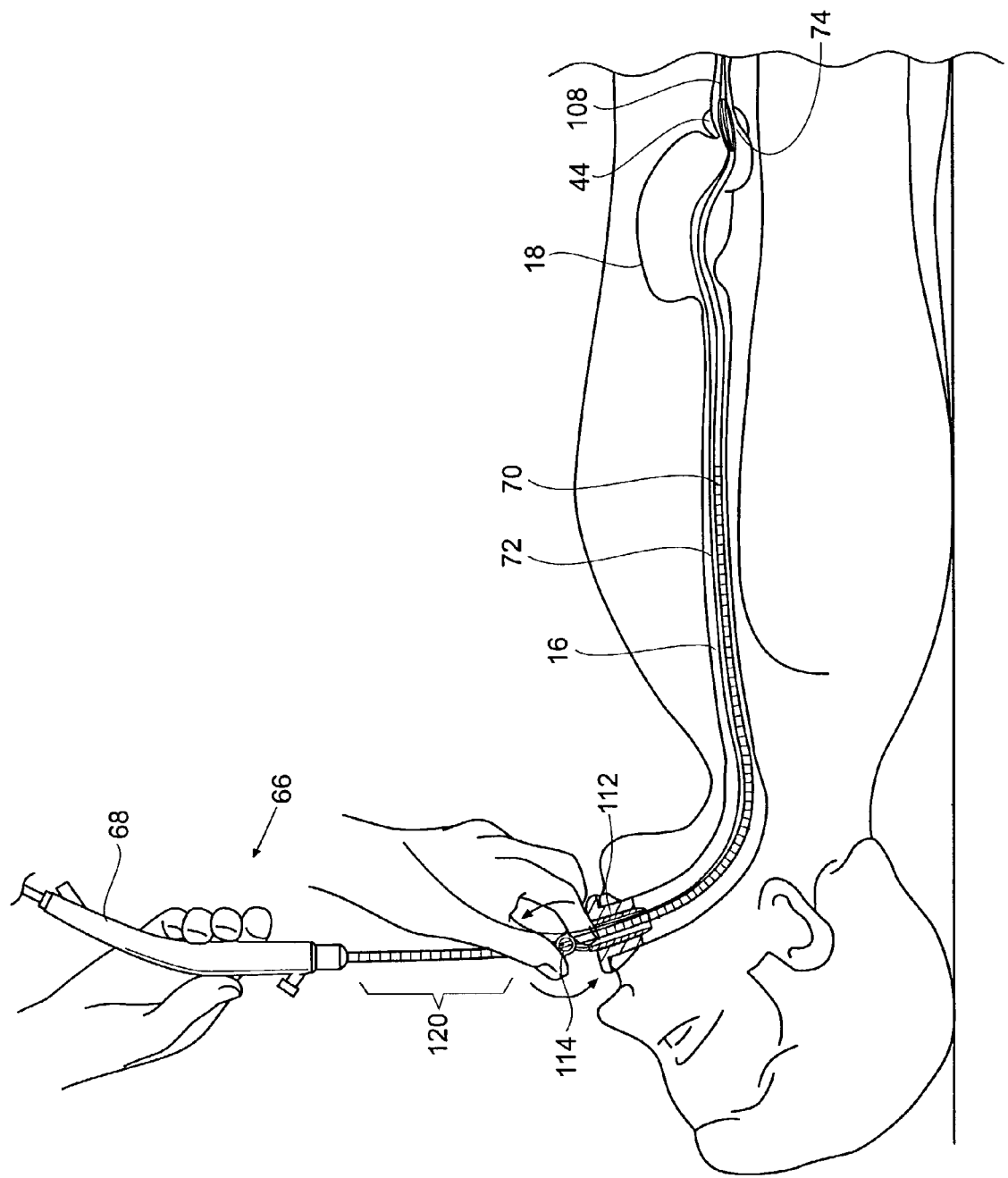

With reference to FIG. 17, after applying the desired amount of radio frequency energy, the electrodes 76 are retracted, e.g., by operation of a push-pull lever on the handle 68 of the device 66. The gripping tool 114 is moved to the open position, thereby enabling the repositioning or removal of the device 66, as desired.

A single series of annular lesions corresponding to the number and position of electrodes 76 on the catheter is thereby formed. It may be that ablation may affect nerves that enervate muscle of the pyloric sphincter 44, thereby resulting in physical shrinkage of the pyloric sphincter 44 and/or affecting nerve pathways. To create greater lesion density in a given targeted tissue area, it may be desirable to create a pattern of multiple lesions, e.g., in rings along the targeted treatment site in the pyloric sphincter 44.

Figure 18:
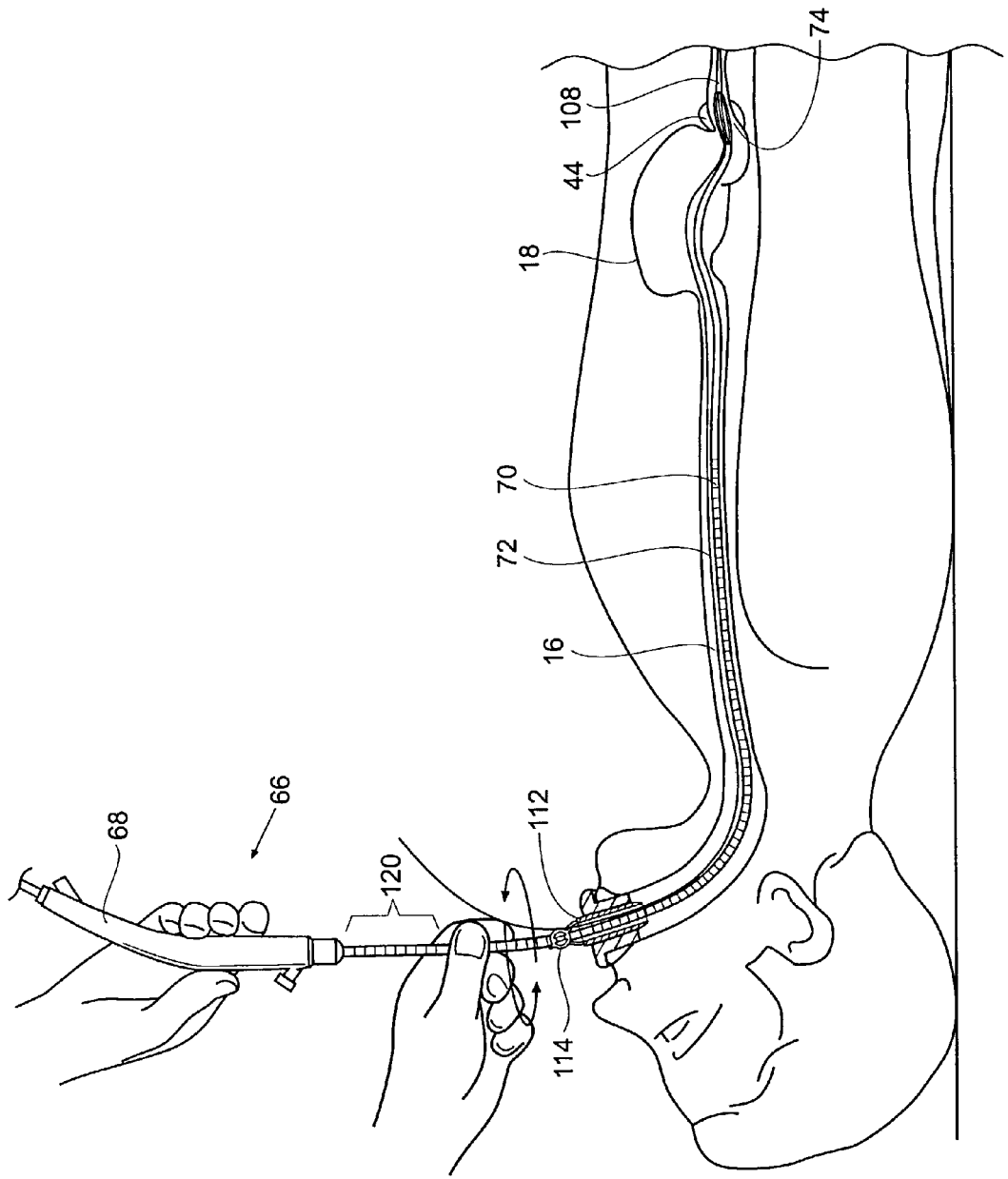

Various lesion patterns can be achieved in the pyloric sphincter 44. A pattern of multiple lesions, created by repositioning the device 66 one or more times after performing an ablation, may be spaced apart along the pyloric sphincter 44. For example, with reference to FIG. 18, with the electrodes 76 retracted and the expandable structure 98 expanded, the device 66 is rotated, the electrodes 76 are then extended again, and RF energy is applied to produce a second series of lesions.

Figure 19:
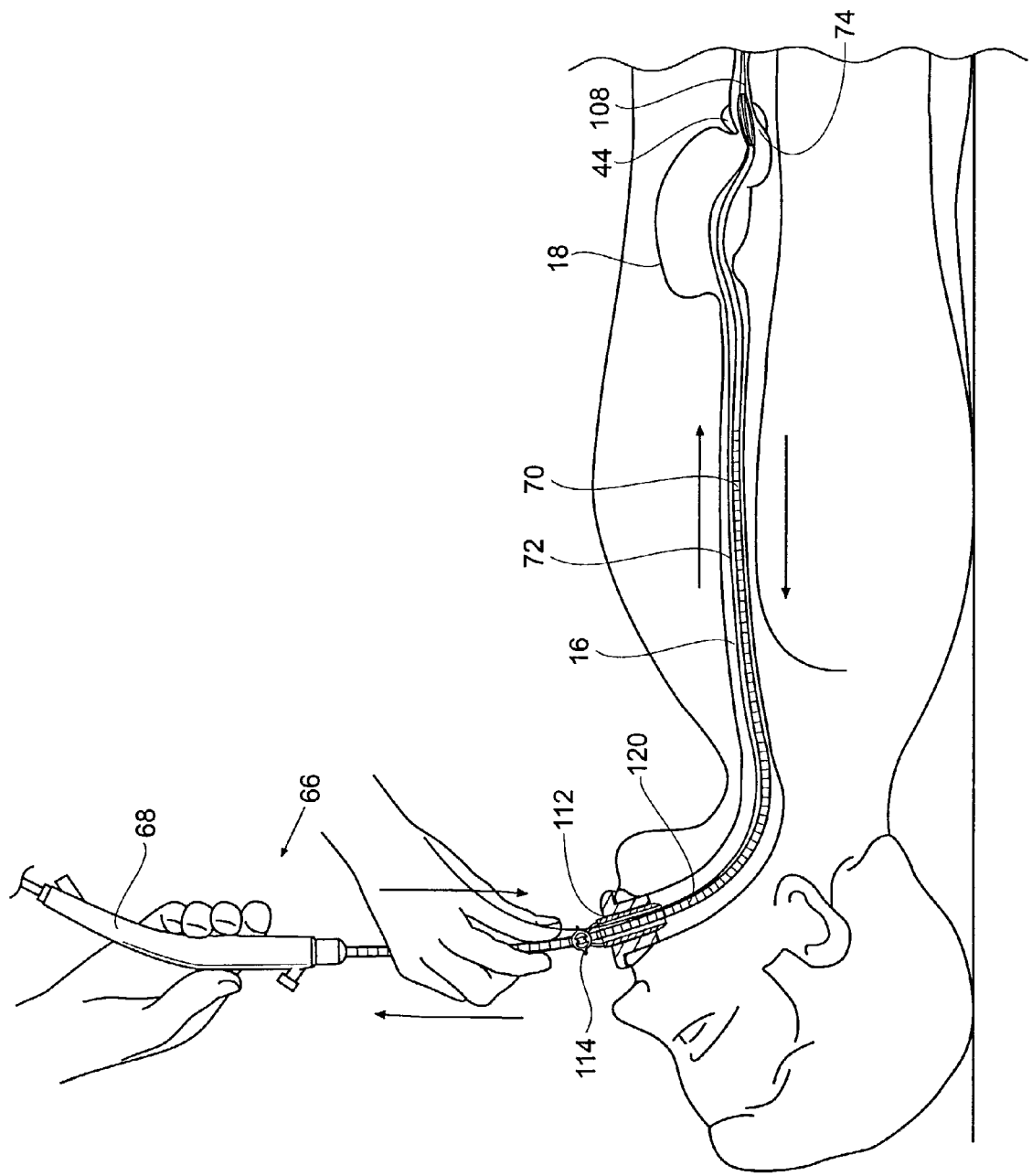

Alternatively, with the electrodes 76 retracted and the expandable structure 98 expanded, the device 66 is moved axially (i.e., advanced or retracted), as seen in FIG. 19, the electrodes 76 are then extended again, and RF energy is applied to produce a second series of lesions. It is to be understood that any number and combination of rotational and axial movements may be performed to produce a desired lesion pattern.

Upon completion of all desired ablation sequences, the electrodes 76 are retracted. The inflatable member 102 is then deflated and the expandable structure 98 is likewise collapsed. The gripping tool 114 is moved to the open position, and the device 66 and bite block 112 are removed.

B. Complementary Magnet Systems

Figure 21:
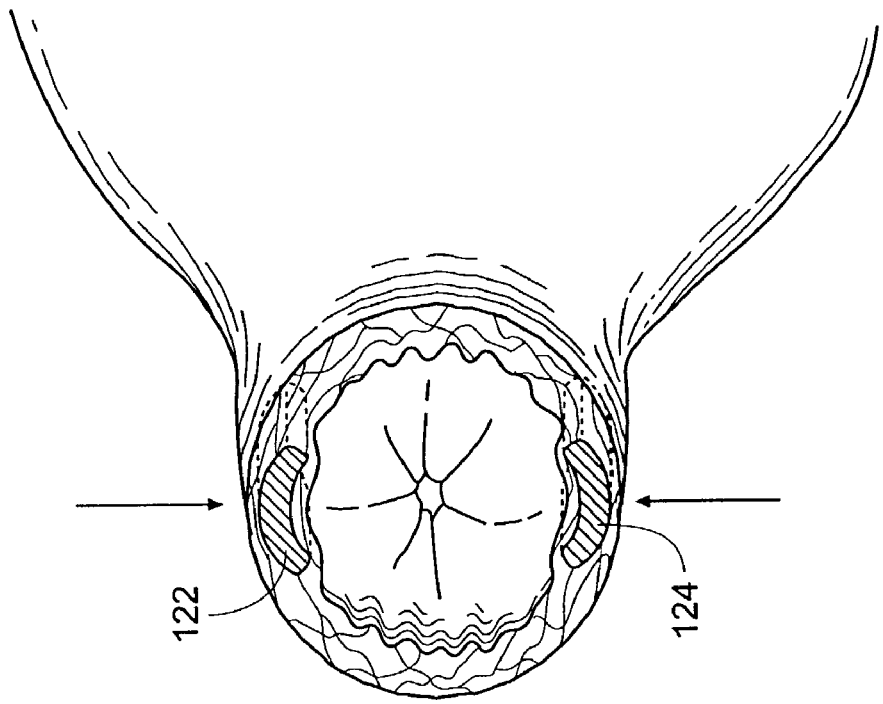
FIGS. 20 and 21 are schematic anatomic views of a pyloric sphincter region showing a magnetic source implanted in the sphincter region that is sized and configured to magnetically attract material implanted in another region of the pyloric sphincter, for the purpose of enhancing sphincter barrier function.
Figure 20:
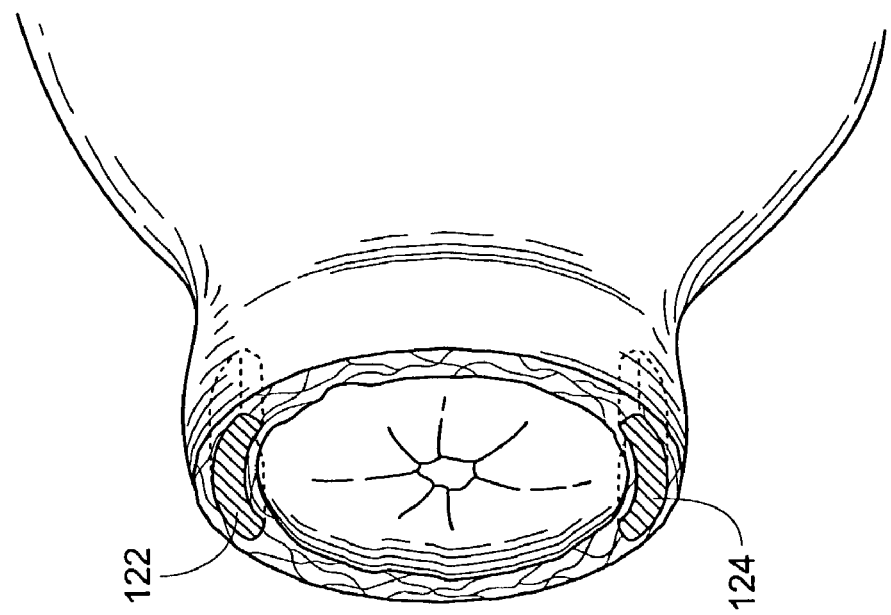

FIGS. 20-21 illustrate an alternative system for tightening the pylorus sphincter 44 using magnetism. More particularly, the system employs a complementary first magnet 122 and second magnet 124 that serve to effect and maintain a preferred location and shape of tissue in the pyloric sphincter 44. FIG. 20 illustrates a pair of first and second magnets 122 and 124 implanted within the tissue of the pylorus 42 on opposing sides. FIG. 21 illustrates the movement of tissue effectuated by attractive magnetic forces between the implanted magnets 122 and 124. By moving and stabilizing tissue in a desired location and shape, the system is able to tighten the pyloric sphincter 44, thereby serving as a treatment for obesity, GERD, and/or Barrett's esophagus.

An object that exhibits magnetic properties (magnetism) is called a magnet. Magnetism is a force of attraction or repulsion between various substances, especially those made of iron and certain other metals, ultimately due to the motion of electric charges. Every magnet has a magnetic field, which is a region around the magnet in which the magnetic effects are observed. In the illustrated embodiment, the magnets 122 and 124 are desirably permanent magnets, i.e., they maintain an essentially constant magnetic field over time.

The magnets 122 and 124 possess poles of opposite polarity. The poles are centers where magnetic attraction is strongest. If the magnet 122 or 124 is free to turn, one pole will point north, and is thus called a North pole, and the opposite pole is likewise called a South pole. According to physical laws, poles of like polarity (North-North or South-South) repel each other with a magnetic force. On the other hand, poles of unlike polarity (North-South or South-North) attract each other with a magnetic force. The force of magnetic attraction or repulsion depends on the strength of the magnets 122 and 124 and the distance between the poles.

In the illustrated embodiment, the first and second magnets 122 and 124 are mutually oriented so that the force of magnetic attraction draws the first and second magnets 122 and 124 toward each other. That is, the first magnet 122 is of opposite polarity from the second magnet 124, e.g., the first magnet 122 is of North polarity and the second magnet 124 is of South polarity, or vice versa. In this Specification, such an orientation of magnetic poles is called "complementary."

It should be appreciated that either magnet 122 or 124 may exert a magnetic force on a material that is not magnetized. Therefore, one of the magnets 122 or 124 can be replaced by a material, e.g., ferrous plate, on which the remaining magnet 122 or 124 is able to exert an attractive magnetic force.

Arranged in a complementary manner, as the magnets 122 and 124 are drawn together, the tissue of the pyloric sphincter 44 is also drawn together, thereby tightening the sphincter 44, as represented by arrows in FIG. 21.

As will be apparent to one skilled in the art, the first and second magnets 122 and 124 can be sized, configured, and placed in a variety of arrangements to effect the desired positioning of tissue.

In the illustrated embodiment, the magnets 122 and 124 provide a concave, or sectorial, configuration, to approximate the contour of the surface of the pylorus 42.

Figure 23:
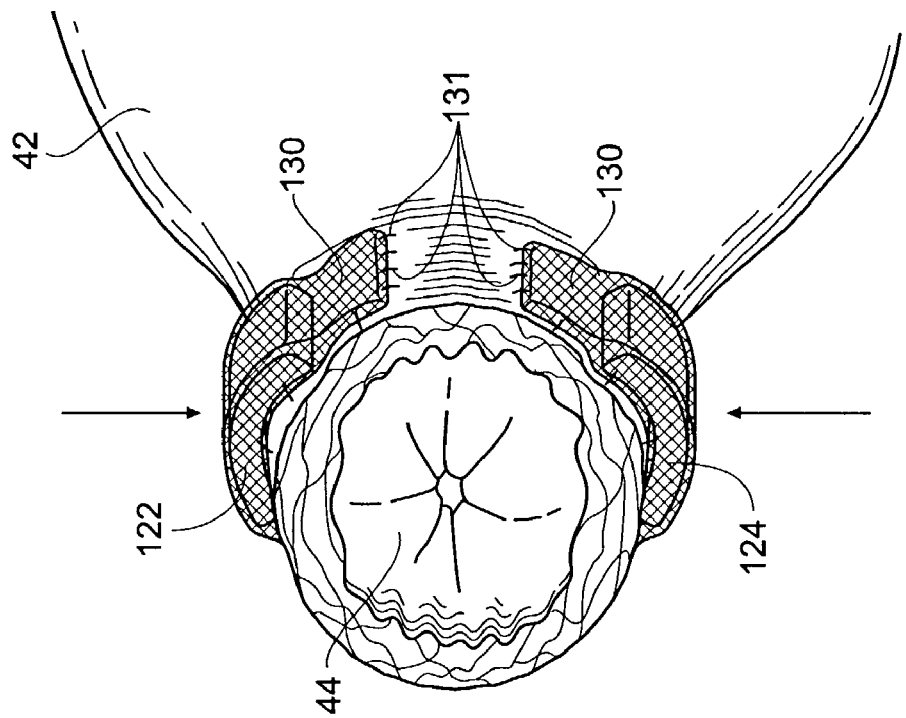
FIGS. 22 and 23 are schematic anatomic views of a pyloric sphincter region showing a magnetic source fitted about an exterior of the sphincter region that is sized and configured to magnetically attract material fitted about an exterior of another region of the pyloric sphincter, for the purpose of enhancing sphincter barrier function.
Figure 22:
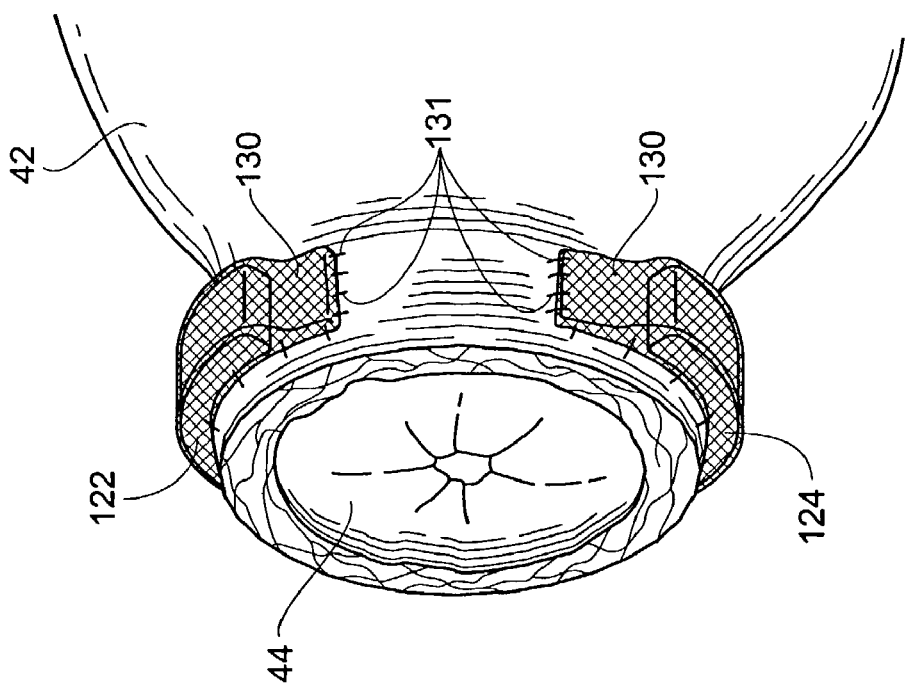

In an alternative embodiment illustrated in FIGS. 22 and 23, the magnets 122 and 124 may be applied within a biocompatible fabric or other suitable matrix 130 that is then attached with sutures 131 to the outside surface of the pylorus 42 on opposing sides, as illustrated in FIG. 22. FIG. 23, as represented by arrows, illustrates the movement of tissue effectuated by attractive magnetic forces between the implanted magnets 122 and 124.

Figure 25:
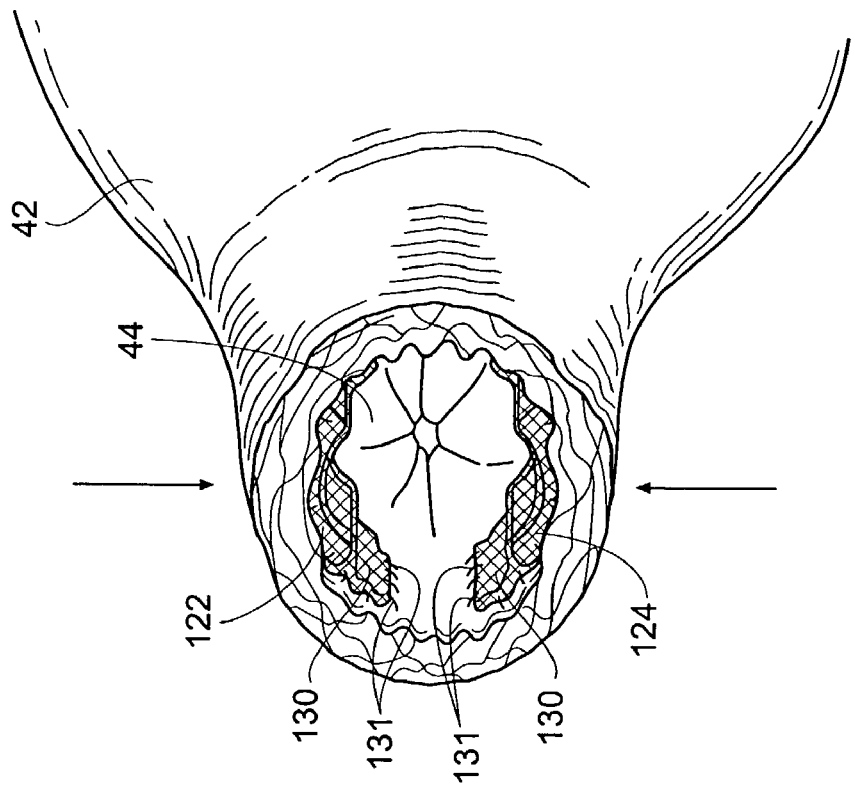
FIGS. 24 and 25 are schematic anatomic views of a pyloric sphincter region showing a magnetic source fitted about an interior of the sphincter region that is sized and configured to magnetically attract material fitted about an interior of another region of the pyloric sphincter, for the purpose of enhancing sphincter barrier function.
Figure 24:
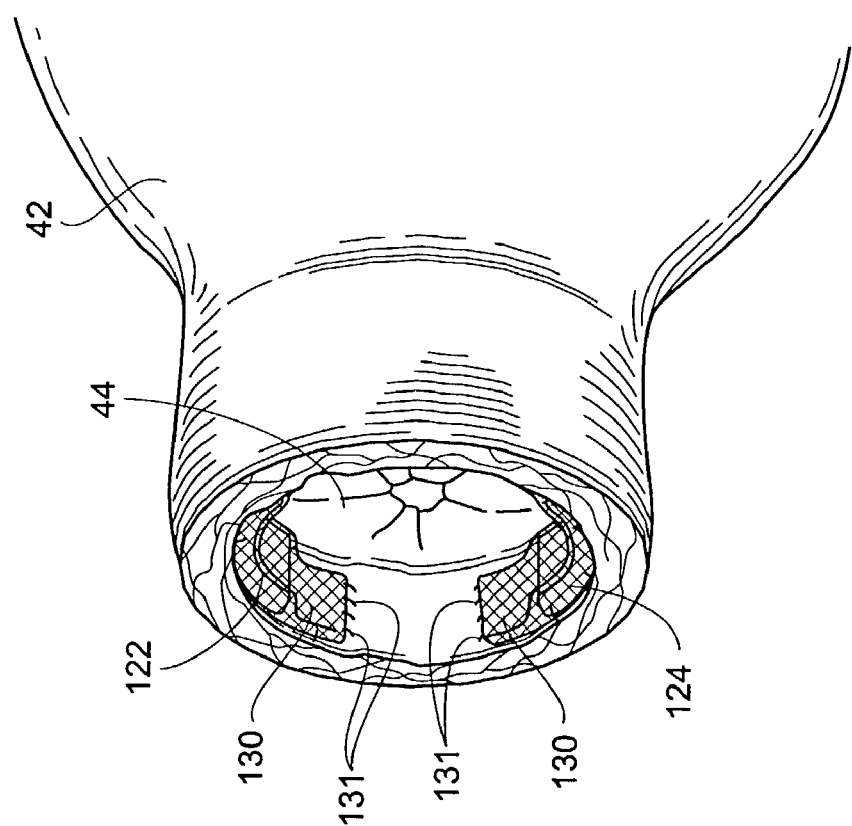

Alternatively, the magnets 122 and 124 may be applied within a biocompatible fabric or other suitable matrix 130 that is then sutured to the inside surface of the pylorus 42 on opposing sides, as illustrated in FIG. 24, to effect movement of tissue as represented by arrows in FIG. 25.

Both implantation and attachment can be done by conventional laparoscopic procedures. Desirably, the magnets 122 and 124 are implanted or attached in an inactivated, i.e., unmagnetized, form. The magnets 122 and 124 may then be activated subsequent to the procedure by exposure to a magnetic field to impart the desired magnetism. When a substance having magnetic properties is placed in a magnetic field (the region surrounding a magnet), the field intensity gives rise to a magnetizing force H within the substance, and the substance acquires a certain magnetization I depending upon H and upon the susceptibility of I/H of the substance.

If desired, the magnets 122 and 124 may be removed by a subsequent surgical procedure, e.g., by laparoscopy. In a preferred embodiment, the magnets 122 and 124 are configured such that they may be selectively inactivated, i.e., demagnetized, after implantation or attachment. Demagnetization results in the loss of magnetic properties.

In the inactivated state, the magnets 122 and 124 are no longer able to effect a tightening of the pylorus 42. Such an arrangement eliminates the need for a subsequent surgical procedure to remove the magnets 122 and 124.

As is apparent to one skilled in the art, the inactivated magnets 122 and 124 can be selectively reactivated, i.e, "remagnetized," by exposure to a magnetic field, as previously described.

C. Pyloric Band

In yet another system for tightening the pylorus 42, a tightening member having a fastening mechanism may be wrapped around the outer circumference of the pylorus 42 to slow gastric emptying and/or reduce biliary reflux. Further, the member prevents overeating by the reducing the maximum capacity of the stomach. It is to be understood that the tightening member and fastening mechanism may be variously constructed.

Figure 26:
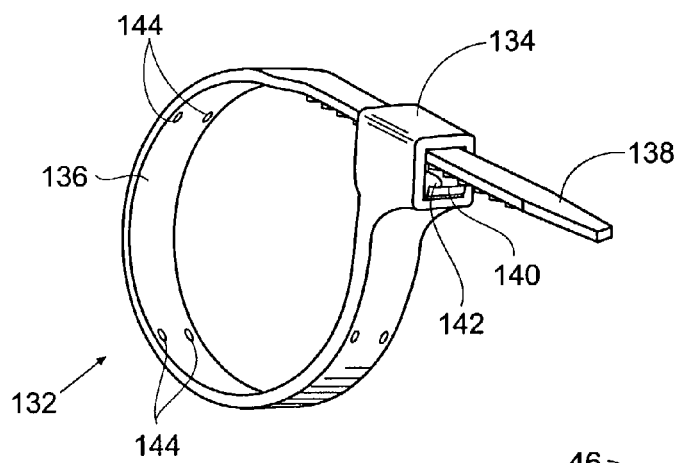
FIG. 26 is a perspective view of one embodiment of band that is sized and configured to be fitted about an exterior of a pyloric sphincter, for the purpose of enhancing sphincter barrier function.
Figure 27:
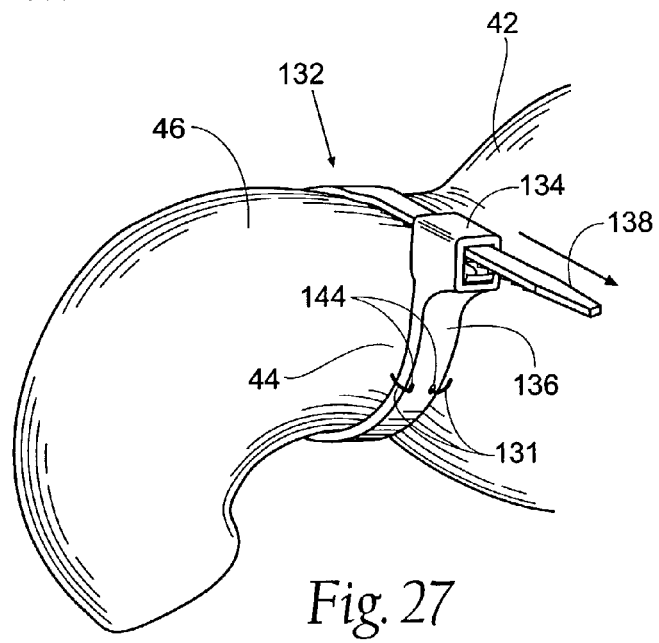
FIGS. 27 and 28 are perspective anatomic views showing the fitment of the band shown in FIG. 26 about a pyloric sphincter.
Figure 28:
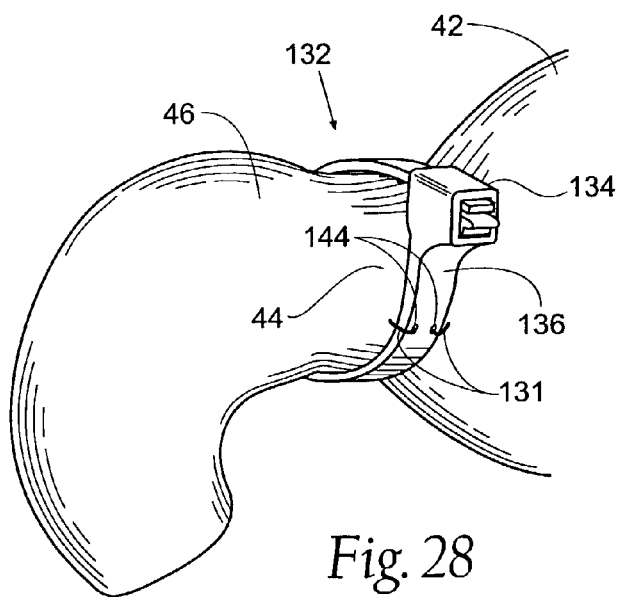

FIGS. 26-28 illustrate one embodiment of such a system in which the tightening member is a band 132 of a cable-tie configuration, permitting the physician to adjust the diameter of the band 132 to fit the individual anatomy of the patient. The band 132 includes a head portion 134, a strap 136, and a tab 138.

The tab 138 is desirably serrated and configured to pass through a slot 140 in the head 134. Advancing the tab 138 through the slot 140 by pulling on the tab 138 decreases the diameter of the band 132. Conversely, reverse movement of the tab 138 through the slot 140 increases the diameter of the band 132. The head 134 can include a locking/releasing pawl 142 to fix and stabilize the band 132 in a desired diameter.

In a preferred embodiment, the strap portion 136 includes suture attachment sites 144, e.g., holes. The suture attachment sites 144 permit the passage of sutures 131 to secure the band 132 to the tissue.

In use, the physician surgically implants the band 132 around the pylorus 42 by conventional laparoscopic procedures. The tab 138 is passed through the slot 140 to provide a diameter effecting a desired tightening of the pylorus 42. The desired position is secured by activation of the locking pawl 142, e.g., by manipulating the tab 138 in an upward direction. If desired, the band 132 is sutured into place using the suture attachment sites 144.

Figure 29:
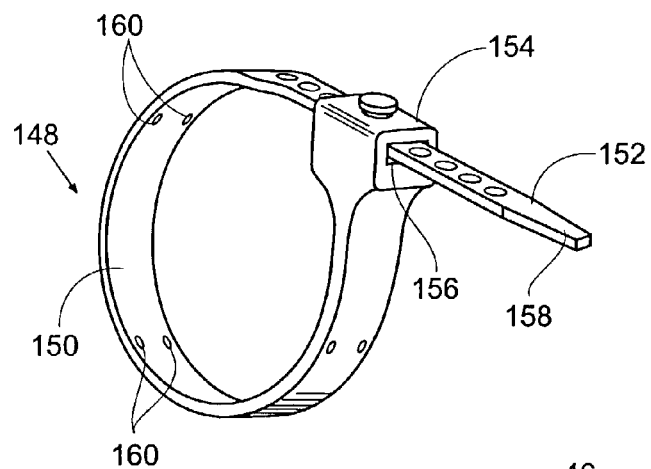
FIG. 29 is a perspective view of another embodiment of band that is sized and configured to be fitted about an exterior of a pyloric sphincter, for the purpose of enhancing sphincter barrier function.
Figure 30:
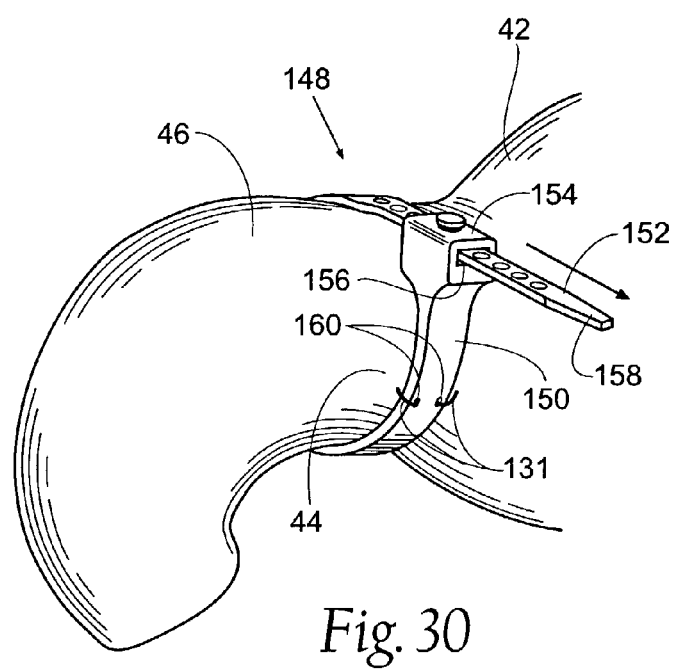
FIGS. 30 and 31 are perspective anatomic views showing the fitment of the band shown in FIG. 29 about a pyloric sphincter.
Figure 31:
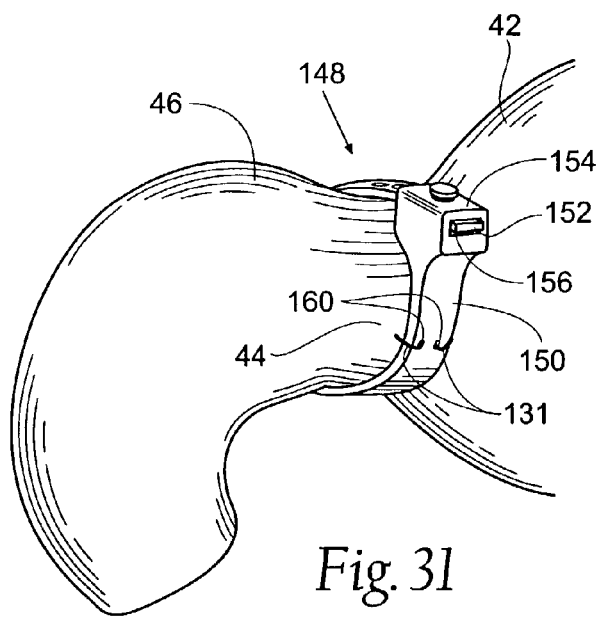

FIGS. 29-31 illustrate another embodiment of such a system in which the tightening member is a band 148 of a belt-like configuration, permitting the physician to adjust the diameter of the band 148 to fit the individual anatomy of the patient. The band 148 includes a body portion 150, a tab 152, and a buckle 154.

The tab 152 is configured to pass through a slot 156 in the buckle 154. The tab 152 desirably includes a tapered end region 158 for ease of passage through the slot 156. Advancing the body portion 150 through the slot 156 by pulling on the tab 152 decreases the diameter of the band 148. Conversely, reverse movement of the body 150 through the slot 156 increases the diameter of the band 148. The body 150 desirably includes a series of holes 159 that mate with the buckle 154 to secure the band 148 in the desired diameter.

In a preferred embodiment, the body portion 150 includes suture attachment sites 160, e.g., holes. The suture attachment sites permit the passage of sutures 131 to secure the band 148 to the tissue.

In use, the physician surgically implants the band 148 around the pylorus 42 by conventional laparoscopic procedures. The tab 152 is passed through the slot 156 and to provide a diameter effecting a desired tightening of the pylorus 42. The desired position is secured by closure of the buckle 154. If desired, the band 148 is sutured into place using the suture attachment sites 160.

In either embodiment, the band 132 or 148 is desirably removable by laparoscopic procedure, thereby avoiding problems associated with long-term constriction of the pylorus 42. Because the band 132 or 148 is removable, it is well-suited for temporary use, e.g., in the initial treatment of morbid obesity.

Regardless of the device used, the tightening of the pyloric sphincter 44 restricts or meters the outflow of chime through the pyloric sphincter 44, thereby retaining the stomach 18 contents for a longer period. This not only creates a physical barrier to eating, but also induces a feeling of satiety that mediates against the urge to over-eat. Restriction of the pyloric sphincter 44 can also serve to reduce or prevent the incidence of bilary reflux and thereby serve to prevent or mediate the effects of exposure of bile to tissue in the stomach 18 or esophagus 16, which can include Barrett's esophagus.

III. Systems and Methods for Inhibiting Receptive Relaxation

Another technical feature includes systems and methods for mediating the receptive relaxation of muscles of the proximal stomach. The mediation of this neurological event inhibits the relaxation of stomach muscles, particularly in the fundus and proximal stomach, to inhibit stretching of the stomach and the attendant increase in stomach volume.

Restricting the capacity of the stomach during food intake prolongs a feeling of satiety during and after eating, and thereby reduces the incidence of overeating, which can lead to obesity and other physiologic conditions.

A. Tissue Treatment Device

Figure 32:
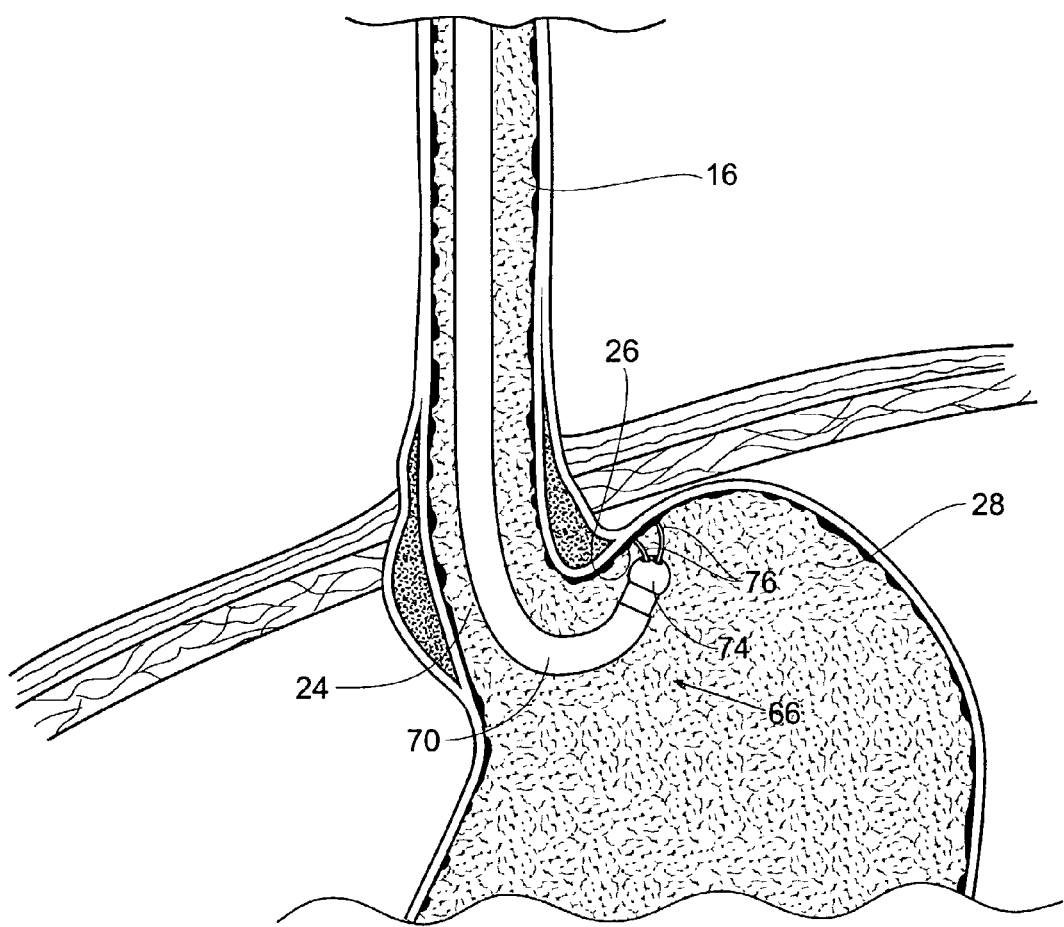
FIG. 32 is a schematic anatomic view of a treatment device for treating a tissue region in the cardia of a stomach that includes a treatment device with a tissue piercing member to inject a treatment agent into the tissue region and/or ablate the tissue region, for the purpose of mediating responsive relaxation of smooth muscle in the stomach.

FIG. 32 shows a tissue treatment device 66 of the type shown in FIG. 3 deployed in a region of the stomach populated by neural receptors, e.g., the cardia 26 (common reference numerals are used). The treatment device 66 includes an operative element 74 carried at the end of a flexible catheter tube 70. The details of deployment of treatment devices into the stomach have been previously described. The physician can introduce the catheter tube 70 and operative element 74 into the cardia 26 through the esophagus 16, with or without the use of a guide wire, as previously described.

In FIG. 32, the operative element 74 includes one or more tissue piercing members 76. As FIG. 32 shows, the operative element carries multiple tissue piercing members 76.

In one treatment modality, the operative element 74 serves to apply ablation energy in a selective fashion through the tissue piercing members 76 to tissue at, in, or near the cardia 26. The application of ablation energy creates one or more lesions, or a prescribed pattern of lesions, below the mucosal surface. The lesions inhibit neurological interaction of the afferent neural receptors with the vagus nerve, by interrupting or moderating afferent neural signals created as food entering the stomach stretch smooth muscle innervated by these receptors. The lesions thereby inhibit or moderate the incidence of further muscle relaxation and stretching in the stomach as a result of receptive relaxation. Surface tissue can be targeted for ablation, or, alternatively, tissue can be targeted for ablation below the surface, including the submucosa. The ablation can be achieved by exposure of the tissue to conductive tissue heating, ohmic tissue heating, or an ablation agent, or combinations thereof.

The systems and methods can also affect the interruption or reduction of receptive relaxation by injection through one or more of the tissue piercing elements 74 of a neural treatment agent in, at, or near regions in the stomach populated by afferent neural receptors, such as the cardia. The neural agent is selected to cause the interruption or reduction of afferent nerve impulses affecting receptive relaxation. The neural treatment agent can comprise e.g., at least one sub-type of a vanilloid-containing compound, as previously described. The injection of the treatment agent can be provided with or without ablation of tissue. The vanilloid-containing treatment agent can be applied to the mucosal lining or extrinsically to the outside of the cardia 26. The vanilloid-containing treatment agent may be applied or injected as primary therapy, or applied as a supplementary treatment before, during or after a primary intervention. Ablation energy may be used to incite a wound, followed by application of the vanilloid-containing treatment agent to facilitate exuberant wound healing.

These treatment modalities, alone or in combination, can thereby mediate the receptive relaxation response to prevent or reduce the incidence of overeating, which can lead to obesity.

B. Complementary Magnetic Matrixes

Figure 35A:
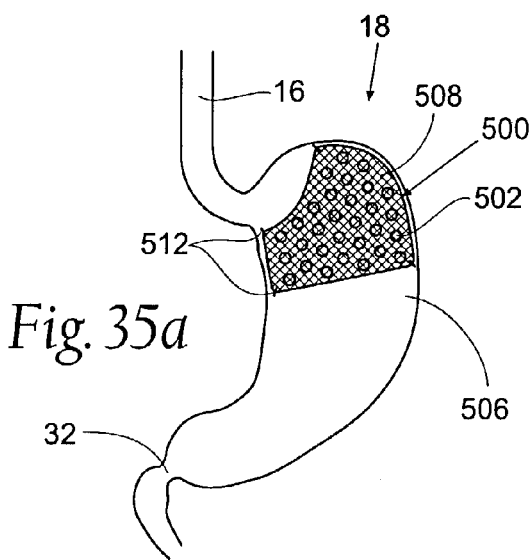
FIG. 35A is a schematic anatomic side view of a stomach after responsive relaxation and stretching during intake of food, showing the presence of a magnetic matrix to resist or moderate the extent of stretching and expansion during intake of food.
Figure 35B:
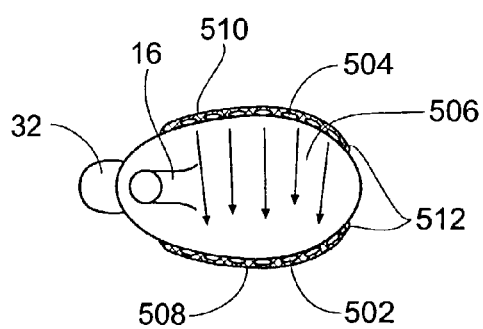
FIG. 35B is a schematic anatomic top view of the stomach shown in FIG. 35A, showing the presence of a magnetic matrix, which (in comparison to FIG. 34B, has served to resist or moderate the extent of stretching and expansion during intake of food.

FIGS. 35A and 35B illustrate an alternative system 500 for moderating the results of receptive relaxation. The system 500 includes first and second matrixes 502 and 504 affixed, respectively, to the anterior and posterior walls of the proximal stomach 506. The first and second matrixes each carried an array of magnets, respectively 508 and 510. The magnets 508 of the first matrix 502 and the magnets 510 of the second matrix 504 possess poles of different polarity (i.e., North-South or South-North). The array of magnets 508 and 510 thereby attract, as shown by arrows in FIG. 35B. The principles of magnetism and magnetic attraction have been previously discussed.

Figure 34A:
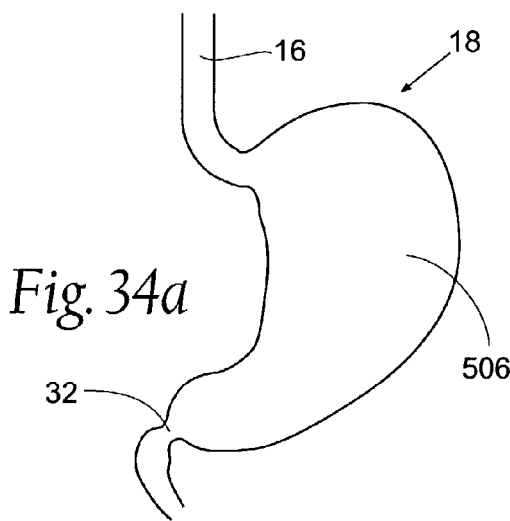
FIG. 34A is a schematic anatomic side view of a stomach after responsive relaxation and stretching during intake of food.
Figure 34B:
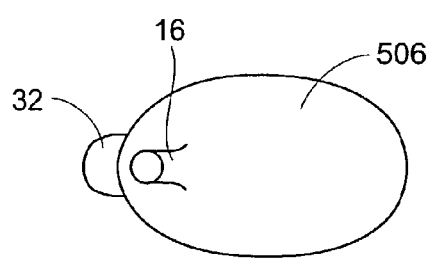
FIG. 34B is a schematic anatomic top view of the stomach shown in FIG. 34A after responsive relaxation and stretching during intake of food.

The force of magnetic attraction between the two matrixes 502 and 504 resists or moderates expansion or stretching of the anterior and posterior walls of the proximal stomach 506 away from each other. As a result, even though the smooth muscle of the proximal stomach may be conditioned by receptive relaxation to expand and stretch to receive food, the force of magnetic attraction generated by the matrixes 502 and 504 physically resist or moderate the expansion. As a result, the matrixes resist or moderate the incidence of further muscle relaxation and stretching in the proximal stomach as a result of receptive relaxation. FIGS. 34A and 34B illustrate the extent of normal stretching as a result of receptive relaxation and intake of food. FIGS. 35A and 35B illustrate the extent of moderated stretching as a result of the forces of magnetic attraction. The matrixes 502 and 504 serve to reduce capacity of the stomach despite receptive relaxation.

Restricting the capacity of the stomach during food intake prolongs a feeling of satiety during and after eating, and thereby reduces the incidence of overeating, which can lead to obesity and other physiologic conditions.

The matrixes 502 and 504 may comprise, e.g., a resilient, biocompatible fabric or other suitable material that can be attached with sutures 512 or the like to anterior and posterior walls of the proximal stomach.

It should be appreciated that either magnetic array 508 and 510 may exert a magnetic force on a material that is not magnetized. Therefore, one of the magnet arrays 508 or 510 can be replaced by a material, e.g., ferrous plate, on which the remaining magnetic array is able to exert an attractive magnetic force.

Both implantation and attachment can be done by conventional laparoscopic procedures. The magnetic arrays 508 and 510 can be attached in an inactivated, i.e., unmagnetized, form. The magnetic arrays 508 and 510 may then be activated subsequent to the procedure by exposure to a magnetic field to impart the desired magnetism.

If desired, the magnetic arrays 508 and 510 may be removed by a subsequent surgical procedure, e.g., by laparoscopy.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A method to treat obesity comprising
   (i) providing an expandable member expandable between a collapsed condition and an expanded condition, the expandable member including at least one energy-delivery electrode movable between a retracted position within the expandable member and an extended position piercing tissue,
   (ii) introducing the expandable member into a pyloric sphincter in the collapsed condition and with the energy-delivery electrode in the retracted position,
   (iii) expanding the expandable member to dilate the pyloric sphincter,
   (iv) moving the energy-delivery electrode into the extended position piercing tissue in, at or near the pyloric sphincter,
   (v) delivering energy through the energy-delivery electrode to ablate tissue in, at, or near the pyloric sphincter to create a first lesion pattern,
   (vi) moving the energy-delivery electrode into the retracted position,
   (vii) axially advancing or retracting the expandable member to reposition the energy-delivery electrode with respect to the pyloric sphincter, and
   (viii) moving the energy-delivery electrode into the extended position piercing tissue in, at or near the pyloric sphincter,
   (ix) delivering energy through the energy-delivery electrode to ablate tissue in, at, or near the pyloric sphincter to create another lesion pattern, and
   (x) repeating (vi) to (ix) until a desired pattern of multiple lesions spaced apart axially along the pyloric sphincter is formed to affect tightening of the pyloric sphincter.

2. A method as in claim 1, further comprising applying a treatment agent in, at, or near the pyloric sphincter.

3. A method as in claim 2 wherein the treatment agent leads to a physical tightening of the sphincter.

4. A method as in claim 3 wherein the treatment agent is a cytokine subtype.

5. A method as in claim 3 wherein the treatment agent is a tissue bulking agent.

6. A method as in claim 2 wherein the treatment agent is selected from a class of agents that interrupt afferent nerve impulses that trigger transient sphincter relaxation.

7. A method as in claim 6 wherein the treatment agent is a vanilloid.

8. A method as in claim 1 wherein the expandable member is introduced using an endoscope.

9. A method as in claim 1 wherein the expandable structure includes an array of tubular spines that form a basket.

10. A method as in claim 9 wherein the expandable structure further comprises an inflatable body within the basket.

11. A method as in claim 10 wherein the inflatable body is a balloon.

12. A method as in claim 9 wherein one of the spines includes a lumen sized and configured for passage of a guidewire.

13. A method as in claim 9 wherein at least one spine includes a lumen sized and configured to convey a cooling liquid.

14. A method as in claim 1, further comprising delivering a cooling fluid in, at, or near the pyloric sphincter.

15. A method to treat biliary reflux comprising
   (i) providing an expandable member expandable between a collapsed condition and an expanded condition, the expandable member including at least one energy-delivery electrode movable between a retracted position within the expandable member and an extended position piercing tissue,
   (ii) introducing the expandable member into a pyloric sphincter in the collapsed condition and with the energy-delivery electrode in the retracted position,
   (iii) expanding the expandable member to dilate the pyloric sphincter,
   (iv) moving the energy-delivery electrode into the extended position piercing tissue in, at or near the pyloric sphincter,
   (v) delivering energy through the energy-delivery electrode to ablate tissue in, at, or near the pyloric sphincter to create a first lesion pattern,
   (vi) moving the energy-delivery electrode into the retracted position,
   (vii) axially advancing or retracting the expandable member to reposition the energy-delivery electrode with respect to the pyloric sphincter, and
   (viii) moving the energy-delivery electrode into the extended position piercing tissue in, at or near the pyloric sphincter,
   (ix) delivering energy through the energy-delivery electrode to ablate tissue in, at, or near the pyloric sphincter to create another lesion pattern, and
   (x) repeating (vi) to (ix) until a desired pattern of multiple lesions spaced apart axially along the pyloric sphincter is formed to affect tightening of the pyloric sphincter.

16. A method as in claim 15, further comprising applying a treatment agent in, at, or near the pyloric sphincter.

17. A method as in claim 16 wherein the treatment agent leads to a physical tightening of the sphincter.

18. A method as in claim 17 wherein the treatment agent is a cytokine subtype.

19. A method as in claim 17 wherein the treatment agent is a tissue bulking agent.

20. A method as in claim 16 wherein the treatment agent is selected from a class of agents that interrupt afferent nerve impulses that trigger transient sphincter relaxation.

21. A method as in claim 20 wherein the treatment agent is a vanilloid.

22. A method as in claim 15 wherein the expandable member is introduced using an endoscope.

23. A method as in claim 15 wherein the expandable structure includes an array of tubular spines that form a basket.

24. A method as in claim 23 wherein the expandable structure further comprises an inflatable body within the basket.

25. A method as in claim 24 wherein the inflatable body is a balloon.

26. A method as in claim 24 wherein one of the spines includes a lumen sized and configured for passage of a guidewire.

27. A method as in claim 23 wherein at least one spine includes a lumen sized and configured to convey a cooling liquid.

28. A method as in claim 15, further comprising delivering a cooling fluid in, at, or near the pyloric sphincter.

* * * * *